(12) United States Patent
Gianotti et al.

(10) Patent No.: US 12,214,147 B2
(45) Date of Patent: Feb. 4, 2025

(54) ANGIOPLASTY BALLOON CATHETER FOR TREATING VASCULAR DISEASE

(71) Applicant: CTI vascular AG, Neuhausen (CH)

(72) Inventors: Marc Gianotti, Wiesendangen (CH); Andreas Bodmer, Windisch (CH); Ulf Fritz, Bargen (CH); Margeta Dragana, Stetten (CH); Michael Jetter, Thayngen (CH); Sabina Silva, Diessenhofen (CH); Stefan Richter, Egling (DE); Adrienne Müller, Winterthur (CH); Johannes Kuhlicke, Dachsen (CH); Lucien Pistol, Rielasingen-Worblingen (DE); Christopher Weisser, Winterthur (CH); Adila Rapkic Fazlija, Marthalen (CH)

(73) Assignee: CTI vascular AG, Neuhausen (CH)

(*) Notice: Subject to any disclaimer, the term of this patent is extended or adjusted under 35 U.S.C. 154(b) by 0 days.

(21) Appl. No.: 18/726,079

(22) PCT Filed: Oct. 27, 2022

(86) PCT No.: PCT/EP2022/080074
§ 371 (c)(1),
(2) Date: Jul. 1, 2024

(87) PCT Pub. No.: WO2023/126091
PCT Pub. Date: Jul. 6, 2023

(65) Prior Publication Data
US 2024/0416090 A1    Dec. 19, 2024

Related U.S. Application Data

(60) Provisional application No. 63/295,991, filed on Jan. 3, 2022.

(51) Int. Cl.
*A61M 25/10* (2013.01)

(52) U.S. Cl.
CPC ... *A61M 25/104* (2013.01); *A61M 2025/1004* (2013.01); *A61M 2025/105* (2013.01)

(58) Field of Classification Search
CPC .... A61M 2025/1004; A61M 2025/105; A61M 25/104; A61M 2025/1043;
(Continued)

(56) References Cited

U.S. PATENT DOCUMENTS

| | | | | |
|---|---|---|---|---|
| 4,983,167 A | * | 1/1991 | Sahota | A61M 25/104 604/101.02 |
| 5,620,457 A | * | 4/1997 | Pinchasik | A61M 25/1002 604/101.01 |

(Continued)

*Primary Examiner* — Theodore J Stigell
(74) *Attorney, Agent, or Firm* — Smith Patent, LLC; Chalin A. Smith

(57) ABSTRACT

In accordance with the present disclosure there is provided an angioplasty catheter system and method for using such angioplasty catheter system that facilitates controllably delivering focalized pressure to complex lesions. The angioplasty catheter comprises an elongated member having a proximal end, a distal end, and at least one lumen extending at least partially through the elongated member, and an inflatable member proximally affixed to the elongated member adjacent to the distal end and in fluid communication with the at least one lumen, the inflatable member having a radius R and including at least two lobes (32,34), the at least two lobes separated from each other by one or more waist portion (44) defined by two legs (91,92) and a waist portion length (37) such that upon pressurization, radial stress around the waist portion is directed away from the vessel wall and focalized into the lesion at an angle about perpendicular to the legs (91,92) of the upper and lower base of the waist portion (44) creating variable directional forces from (Continued)

to (70,73) to (70', 73') resulting in the preferential formation of lesion fractures at the waist of the inflatable member.

29 Claims, 21 Drawing Sheets

(58) Field of Classification Search
CPC .. A61M 2025/1052; A61M 2025/1059; A61M 2025/1086; A61M 2025/1015; A61M 25/1011; A61M 25/1006; A61B 2017/22051

See application file for complete search history.

(56) References Cited

U.S. PATENT DOCUMENTS

| | | | | |
|---|---|---|---|---|
| 5,674,192 | A | * | 10/1997 | Sahatjian .......... A61M 16/0481 604/28 |
| 5,976,106 | A | * | 11/1999 | Verin .................... A61N 5/1002 600/3 |
| 2002/0032406 | A1 | * | 3/2002 | Kusleika ............ A61M 25/1011 604/101.02 |
| 2007/0078433 | A1 | * | 4/2007 | Schwager ........... A61M 25/104 604/500 |
| 2014/0358176 | A1 | | 12/2014 | Wantink et al. |

\* cited by examiner

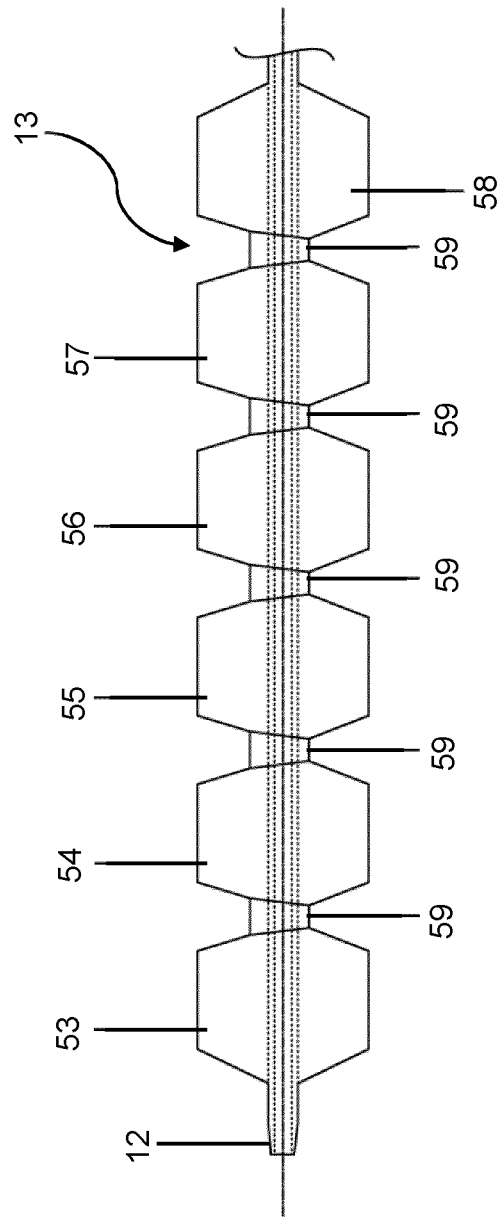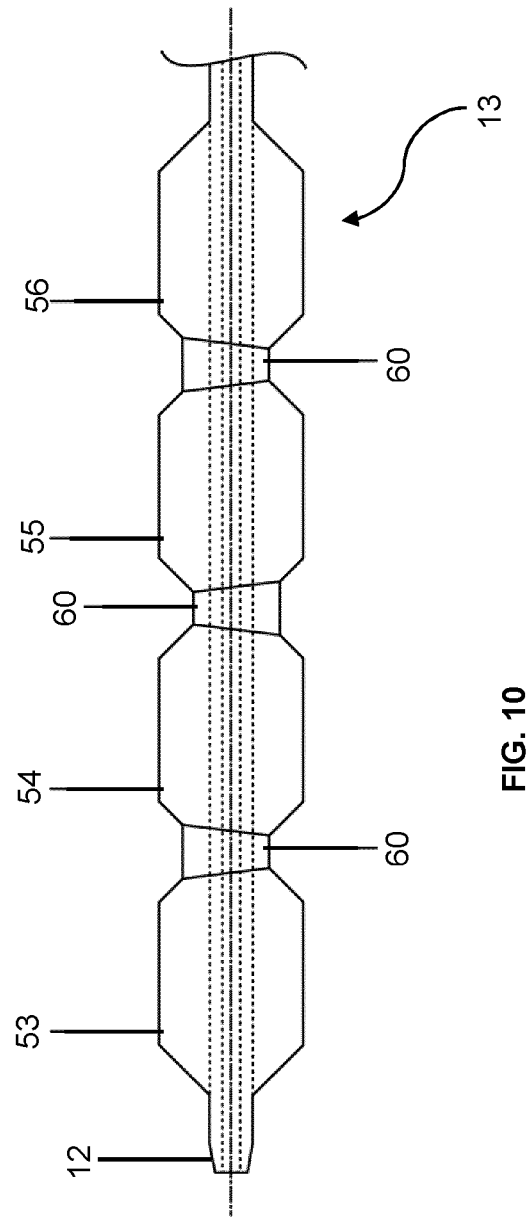
FIG. 9
FIG. 10

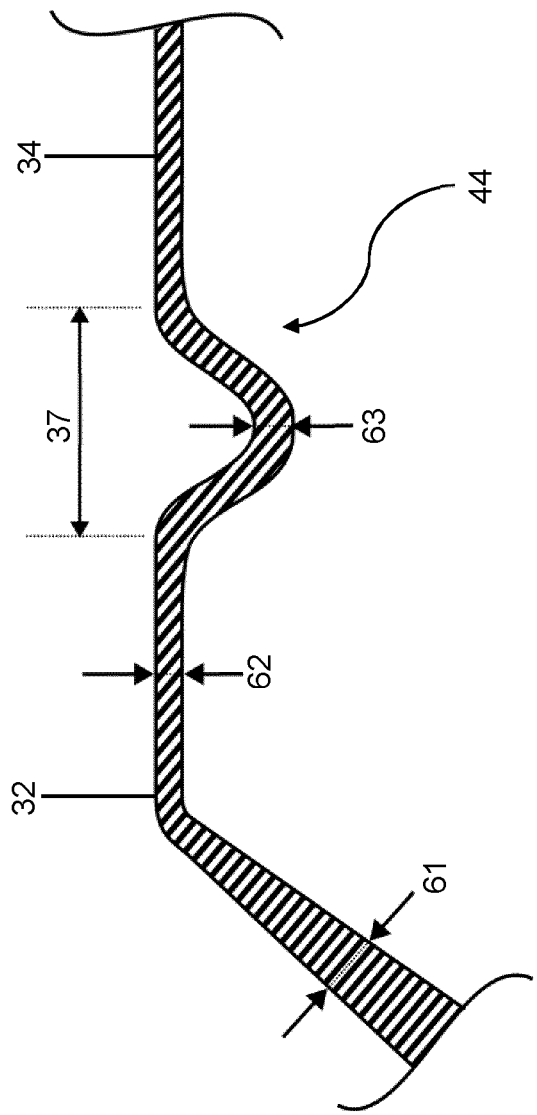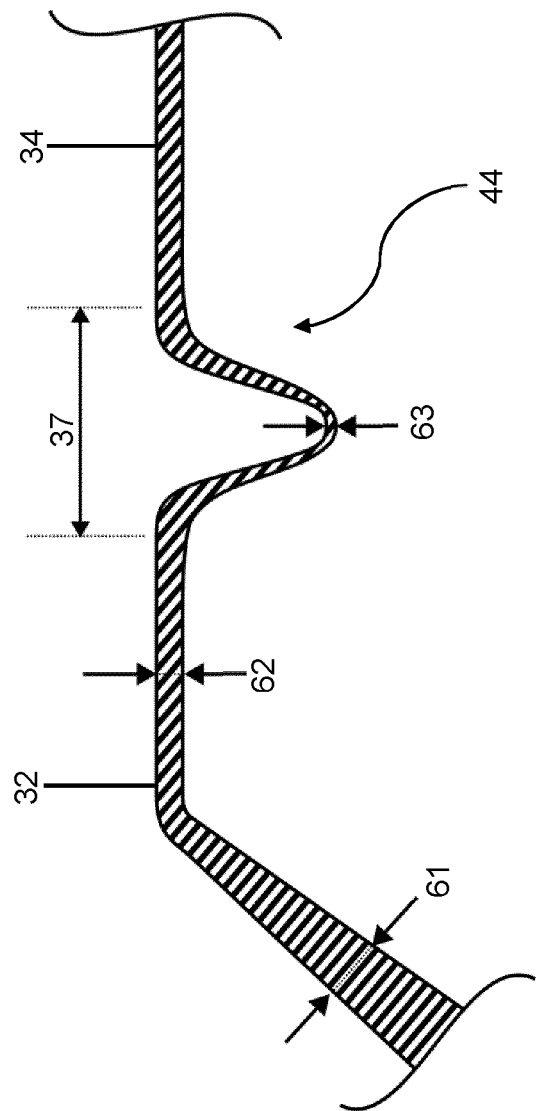
FIG. 11

FIG. 16D
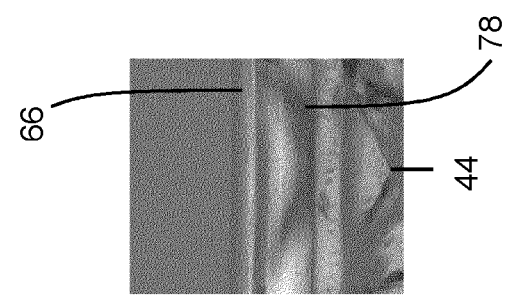
FIG. 16C
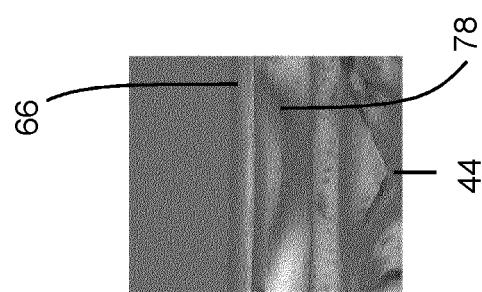
FIG. 16B
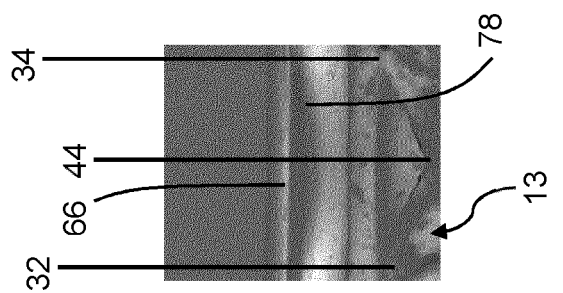
FIG. 16A
FIG. 16

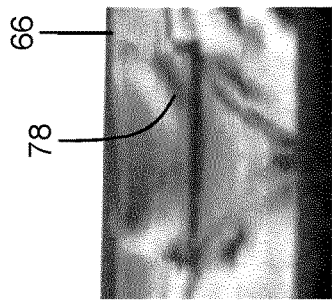
FIG. 17D
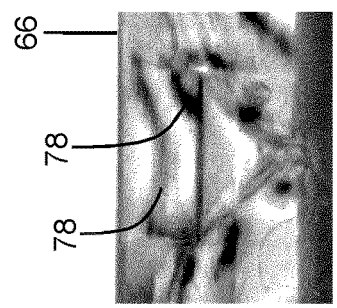
FIG. 18D
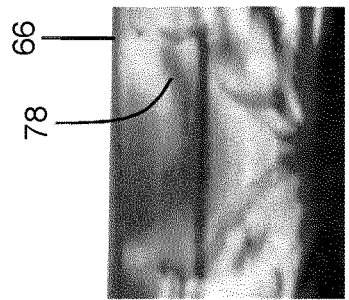
FIG. 17C
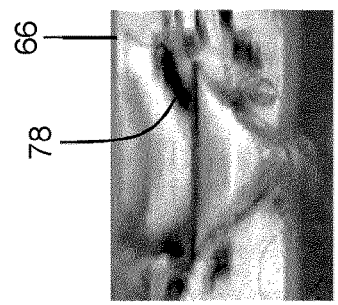
FIG. 18C
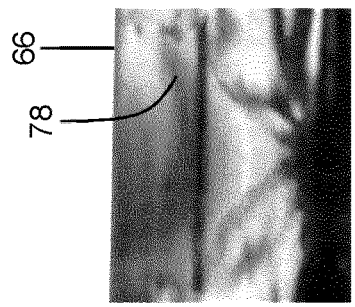
FIG. 17B
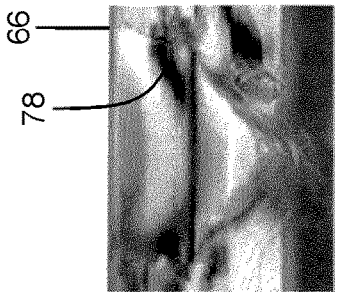
FIG. 18B
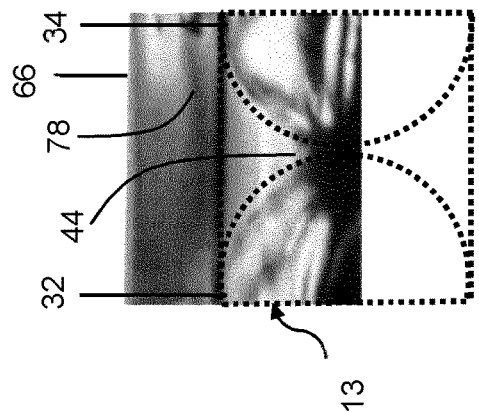
FIG. 17A
FIG. 17
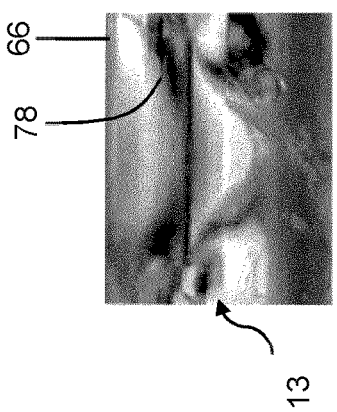
FIG. 18A
FIG. 18

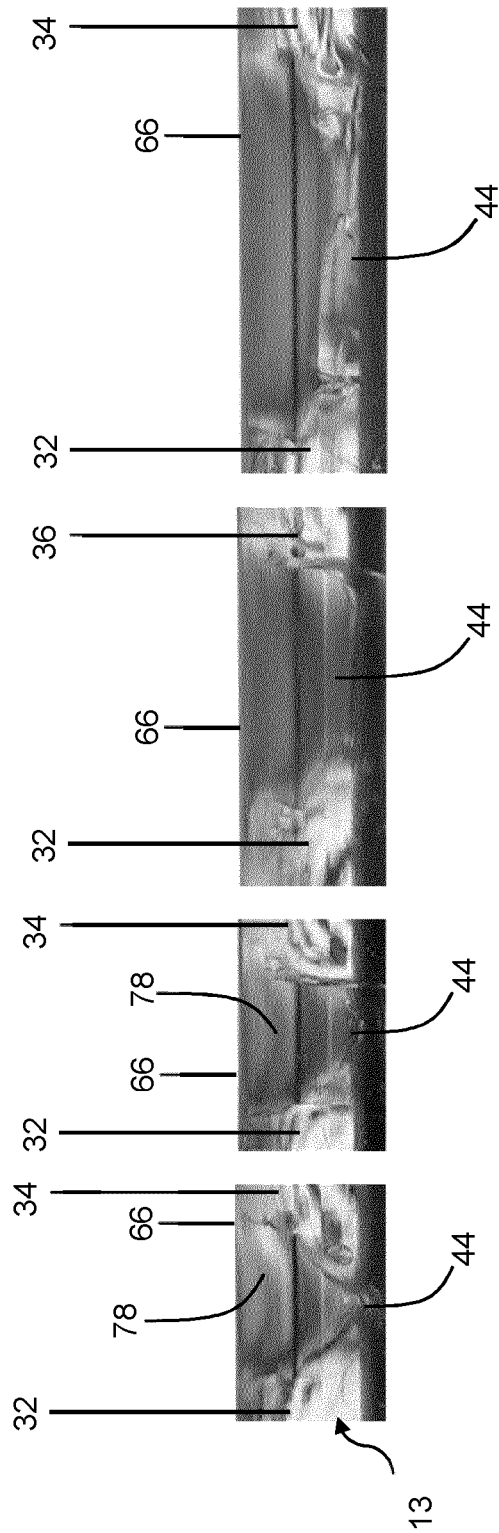

ANGIOPLASTY BALLOON CATHETER FOR TREATING VASCULAR DISEASE

CROSS-REFERENCE TO RELATED APPLICATIONS

This application corresponds to the U.S. National Stage of PCT Application No. PCT/EP22/080074, filed Oct. 27, 2022, which, in turn, claims priority to U.S. provisional application 63/295,991, filed on Jan. 3, 2022, both of which are hereby incorporated by reference in their entirety.

TECHNICAL FIELD

The current disclosure is directed to medical devices and methods of using such devices in the therapeutic treatment of vascular disease. More specifically, the present disclosure is directed to angioplasty balloon catheters, comprising uniquely configured inflatable members that enable enhanced modes of device-tissue interaction. In particular, the invention relates to an angioplasty balloon catheter comprising an elongated member having a proximal end, a distal end and at least one lumen extending at least partially through the elongated member; and an inflatable member proximally affixed to the elongated member adjacent to the distal end and in fluid communication with the at least one lumen, the inflatable member having a radius R and including at least two lobes, the at least two lobes separated from each other by one or more waist portion. The devices of the present disclosure can be operated by static or pulsatile pressure means to enable three dimensional plaque modification through a controllable multi-fracture mode for further medical use in complex lesion treatment and for intramural drug delivery.

BACKGROUND

Angioplasty techniques involve the use of a balloon catheter which is inserted into the patient's vessels through an access point for example in the femoral, subclavian, radial or brachial arteries. The balloon is advanced and positioned by guiding the catheter over a guide wire so that the balloon portion of the catheter is placed in the target region of treatment. The balloon is subsequently inflated, typically utilizing a mixture of saline and contrast agent applied to the inflation port of the balloon catheter, to controllably expand the balloon within the lesion, break up and push the lesion into the vessel wall and, subsequent to deflation and removal of the device, re-enable patency and thus blood flow within the target vessel. In order to treat lesions effectively, a physician first chooses an appropriately sized balloon catheter in relation to the target lesions' dimensions and consecutively advances the balloon to the lesion to be treated. The balloon is then inflated at rates and pressure ranges suitably determined by the physician, which, depending on the individual clinical diagnosis, can typically range between 6 to around 30 bar of applied inflation pressure, or even higher. During the inflation procedure, the appropriately positioned balloon transmits a radial force dependent on the inflation pressure resulting in a dimensional change applied to a designated target area of the vessel, such as a lesion. The efficacy of the procedure foreseeably depends on multiple factors, including the three-dimensional lesion morphology, lesion composition and degree of calcification, ratio of balloon and vessel diameter, balloon expansion behavior and compliance, balloon geometry, contact area formed between balloon and lesion, amount of pressure exerted by the balloon, pressurization rate and dwell time in the lesion, among others.

A conventional balloon is typically formed as a single, elongated tubular member. In its initial state prior to inflation, the balloon is provided folded and pleated to minimize crossing profile. When the balloon is inflated, the balloon pleats unfold, applying a torsional load to balloon and vessel. The elongated tubular member responds to the further application of pressure through a change of radial diameter and a change of axial length. Unfolding, as well as change of radial and axial balloon dimensions progress at different rates and substantially take effect at different stages into the inflation procedure. Axial balloon growth will occur predominantly after the radial expansion of the balloon has been substantially completed. The expansion of a conventional balloon during angioplasty therefore not only results in a desired radial expansion, but also in an undesired formation of torsional-, shear-, and/or axial stress on the surrounding vessel wall. Radial stress, exemplarily caused by over-inflation of the balloon and/or application of exceedingly high pressures can result in undesirable persistent distention of a blood vessel which, in turn, may disrupt laminar blood flow within and near the distention and lead to regrowth of the treated lesion or the formation of new lesions. Localized forces produced by balloon inflation can also induce fissures and tears in the inner blood-vessel-wall lining that result in blood flow into a false lumen, or channel, between blood-vessel-wall, referred to as "dissection." A dissection occurs when a portion of the plaque, including intima, is lifted away from the vessel wall and does not remain adherent. The portion of the plaque that has been disrupted by dissection may then protrude into the vessel lumen. When the plaque completely lifts from the vessel wall, it can further impede blood flow, cause acute occlusion of the blood vessel, or trigger an embolic event further downstream of the treatment site. In more serious cases, these localized forces may result in a rupture, hematoma or pseudo-aneurysm. Axial stress can cause an unfavorable proximal and/or distal distension of healthy tissue adjacent to the lesion. Because healthy, soft tissue responds more readily to the application of stress as compared to diseased, hardened and/or calcified tissue, the resulting axial strain may cause undesired dissections and ruptures proximal and distal to the lesion. Torsional- and/or shear stress on the other hand applies tangential forces to the lesion and/or vessel wall along the entire length of the balloon, which can abrade the lesion, damage the vessel, weakening the vessel wall and thereby, further exacerbate the formation of dissections and ruptures.

Because angioplasty balloons are commonly non-compliant or semi-compliant, such balloons are comparatively rigid and exhibit relatively poor flexibility and/or conformability to curved vessel anatomies. The expansion of conventional angioplasty balloons is therefore frequently accompanied by a tendency of the balloon to straighten-regardless of the underlying vessel morphology. The straightening effect is particularly exacerbated in tortuous anatomies, and can result in undue bending or straightening stress on the vessel during the angioplasty treatment. In addition, a conforming contact surface between the lesion and balloon cannot in all circumstances be reliably established. Accordingly, when the balloon lacks conformal contact to the vessel to be treated, there is an inherent risk, that the vessel cannot be uniformly dilated, that balloon expansion forces are uncontrollably released, and/or that the balloon position becomes unstable. In addition, when semi-compliant or non-compliant balloons are inflated against an eccentric lesion, or when a portion of the plaque is more resistant to dilatation than the remainder of the plaque, the balloon has a tendency to follow the path of least resistance, thereby forcing the unconstrained portions of the balloon to expand first. Yet still, because softer tissue can be more easily displaced as compared to a calcified lesion, undesired dissections and ruptures may occur at the lesion-tissue interface. Further, because complex lesions can generally be heterogeneous in nature, balloon expansion may proceed in a non-uniform manner, wherein the depth, direction, location and number of the lesion fracture(s) cannot be reliably controlled.

While conventional balloon dilation catheters can perform sufficiently well to adequately treat moderate forms of vessel narrowing and obstruction, frequently lesions can be situated in more tortuous vessel paths or present themselves as 'complex lesions', or both, where a hardened plaque situated in the vessel is increasingly impenetrable or hardened due to calcification, such that the lesion cannot be effectively reached, dilated, modified or broken with a conventional angioplasty balloon. In such circumstances, other types of specialized medical devices and procedures have been developed that can be applied with a comparably greater likelihood of procedural success. Such devices and methods may include for example high-pressure balloon angioplasty procedures, as well as so-called 'cutting' or 'scoring' balloons. A cutting or scoring balloon is a balloon catheter which includes cutting or scoring elements that are typically mounted onto the balloons outer surface. When the cutting or scoring balloon is inflated, the cutting or scoring elements act as stress concentrator sites that concentrate the backpressure generated by the balloon and directly focus them onto the target lesion surface, which can result in a more effective way to facilitate the desirable breaking of the lesion/plaque upon inflation of the balloon. Regarding aforementioned devices and methods, high pressure balloon angioplasty can be traumatic to the vessel walls and is frequently accompanied by vessel wall dissections, which may require placement of stents or immediate surgical intervention. Procedurally, the higher the pressure of balloon angioplasty and the more rapidly the target pressure is approached, the risk for more severe dissection is increased. In comparison, cutting or scoring balloons can be expanded at lower pressures than high pressure balloon angioplasty, and the focused forces of the cutting or scoring elements can directly penetrate the vessel wall including the lesion. Because the deployment of cutting-, or scoring balloons is accompanied by torsional- and/or shear stress e.g. due to balloon unfolding during expansion, and because the cutting-, or scoring elements come in contact with the vessel wall by design, the risk of generating undesired vessel wall damage and/or dissections is inherently higher than compared to conventional and high pressure angioplasty balloons. Damage or injury to the vessel wall will not only promote the adherence of blood cells passing through the vessel at the point of injury, which can lead to acute thrombotic occlusions in the short term, but also promote restenosis in the long-term, thereby necessitating eventual re-intervention. In turn, vessel trauma, dissections and recoil may contribute to poor long term clinical results and restenosis even if a stent is placed in the treated lesion.

Taken together, current angioplasty balloon catheter systems and available angioplasty treatment procedures exhibit at least one or more of the following deficiencies or problems:

a) lack of adequate axial flexibility, due to single body balloon construction, resulting in lack of conformal contact between balloon, vessel and lesion;

b) lack of positional stability, due to lack of conformal contact and tendency to straighten;

c) lack of adequate axial and/or radial stability and/or compliance, due to single body balloon construction, resulting in length and/or diameter mismatch between target vessel and/or lesion;

d) lack of torsional stability, due to presence of surface features, such as balloon folds, and cutting,—or scoring elements along the length of the entire balloon that apply a torsional load on vessel and/or lesion during inflation of the balloon;

e) lack of control in delivering focalized pressure to complex lesions due to design factors including balloon geometry, balloon expansion behavior and axial, radial and/or torsional stability or compliance, and lack of contact area formed between balloon and lesion; and f) lack of control over achieving efficient modulation, modification, and/or fracture of target lesions and plaques due to procedural factors, including the amount of pressure exerted by the balloon, pressurization rate and dwell time in the lesion, wherein these limitations contribute to a lack of uniform lesion fracture, such that the depth, direction, location and number of the lesion fracture(s) cannot be reliably controlled and/or an adequate patency of the vessel cannot be reliably achieved. Therefore, procedural inefficiencies and limitations continue to exist due to the inherent limitations in product design and patient anatomical complexities. There is an unmet need to provide improved medical devices and methods for treating vascular disease, including complex lesions.

In view of the above considerations it is desirable to provide an improved angioplasty catheter system and method for using such angioplasty catheter system that facilitates controllably delivering focalized pressure to complex lesions without having the limitations or drawbacks of the known angioplasty catheter systems. In particular, it is desirable to provide an angioplasty catheter system and method for using such angioplasty catheter system, wherein an application of focalized pressure to a lesion results in a controllable fracture of the lesion at preferably multiple locations. Further, it is desirable to provide an improved angioplasty catheter system and method for using such angioplasty catheter system that flexibly adapts to the three dimensional morphology of a lesion, resulting in maximized conformal contact to a lesion, while maintaining enhanced axial, radial, and/or torsional stability or compliance. Yet still, it is desirable to provide an angioplasty catheter system and method for using such angioplasty catheter system that facilitates an efficient and selective modulation, modification, and/or fracture of target lesions at substantially lower pressure ranges compared to conventional angioplasty catheters and associated angioplasty procedures, that in turn result in the reduction of trauma while enabling a safe and clinically more effective treatment of the patient. Finally, it is desirable to provide an improved angioplasty catheter system and method for using such angioplasty catheter system that facilitates an interactively controllable, intramural drug delivery application prior to, during or after performing an interventional procedure, using static or pulsatile pressure means.

Certain catheter systems are disclosed in the following prior art documents. However, none of the known catheter systems comprise the certain combination of features of the catheter system of the present disclosure and, therefore, none of the known systems solve the above described problems.

RELATED PRIOR ART

Segmented, notched, multi-lobed and/or multiple, individual balloons are generally known in the art. For example, U.S. Pat. No. 4,983,167 teaches a multi-lobed dilatation balloon that readily deforms to assume the shape of the artery, so that acute bends can be dilated without substantial risk of straightening out the artery. The individual balloon lobes are substantially spherical or dumbbell-shaped. U.S. Pat. No. 5,395,333 teaches a multi-lobed perfusion balloon catheter, wherein a plurality of independent balloon lobes extends from the catheter body to engage a vessel wall and are oriented so as to form a flow passage to allow blood to perfuse the vessel. U.S. Pat. No. 7,658,744 teaches a balloon catheter with multiple balloons, wherein at least one of the balloons may include at least one blade. The one or more blades are not formed along the entire length of a balloon so as to achieve greater flexibility. U.S. Pat. No. 6,761,734 teaches a segmented balloon catheter for stenting bifurcation lesions, wherein the segmented balloon catheter comprises an elongated shaft, and first and second cylindrical balloon portions mounted on the distal end of the shaft, which are secured and sealed to the shaft. The segmented balloon catheter remedies the problem of delivering and deploying a stent at or adjacent a bifurcation in a blood vessel. U.S. Pat. No. 6,022,359 teaches a surgical stent positioning and radial expansion system that features a balloon having an outer surface that is broken into separate sections axially spaced from each other by notches, and a segmented stent having flexible links that conform with the structural details of the balloon. The notches can more readily flex axially resulting in the balloon to more easily conform to tortuous arterial pathways. When the stent is radially expanded, the balloon can radially expand the stent with a minimal tendency to straighten. In the cited prior art, the balloon segments, lobes or notches achieve the technical effect of axial flexibility. However, none of the prior art teaches an angioplasty catheter according to the present disclosure, wherein the depth, direction, location and number of the lesion fracture(s) is reliably controlled, and wherein the devices are operated by static or pulsatile pressure means that enable three-dimensional plaque modification and multi-fracture for further medical use in complex lesion treatment and for intramural drug delivery.

The present inventors now found that the above problems can be solved an angioplasty catheter system and method for using such angioplasty catheter system that facilitates controllably delivering focalized pressure to complex lesions by providing an angioplasty balloon catheter comprising an elongated member having a proximal end, a distal end, and at least one lumen extending at least partially through the elongated member; and an inflatable member proximally affixed to the elongated member adjacent to the distal end and in fluid communication with the at least one lumen, the inflatable member having a radius R and including at least two lobes, the at least two lobes separated from each other by one or more waist portion.

SUMMARY

In accordance with the present invention there is provided an angioplasty balloon catheter comprising an elongated member having a proximal end, a distal end, and at least one lumen extending at least partially through the elongated member; and an inflatable member proximally affixed to the elongated member adjacent to the distal end and in fluid communication with the at least one lumen, the inflatable member having a radius R and including at least two lobes, the at least two lobes separated from each other by one or more waist portion.

BRIEF DESCRIPTION OF THE DRAWINGS

FIGS. 4-10 illustrate cross-sectional views of an inflatable member of the angioplasty balloon catheter in accordance with the present disclosure.

FIG. 11A and FIG. 11B illustrate cross-sectional views of a waist portion of the inflatable member manufactured by balloon blowing and/or thermoforming in accordance with the present disclosure.

FIGS. 16A-16D are polariscope images illustrating the stress distribution in a lesion resulting from different amounts of pressurization of the inflatable member in accordance with the present disclosure.

FIGS. 17A-17D are polariscope images illustrating the stress distribution in a lesion resulting from different amounts of pressurization of an inflatable member manufactured by balloon blowing in accordance with the present disclosure.

FIGS. 18A-18D are polariscope images illustrating the stress distribution in a lesion resulting from different amounts of pressurization of an inflatable member manufactured by balloon blowing and thermoforming in accordance with the present disclosure.

FIGS. 19A-19D are polariscope images illustrating the stress distribution in a lesion resulting from a variation of the waist portion length at equal amounts of pressurization of the inflatable member in accordance with the present disclosure.

DETAILED DESCRIPTION

Angioplasty Catheter System

Figure 1:
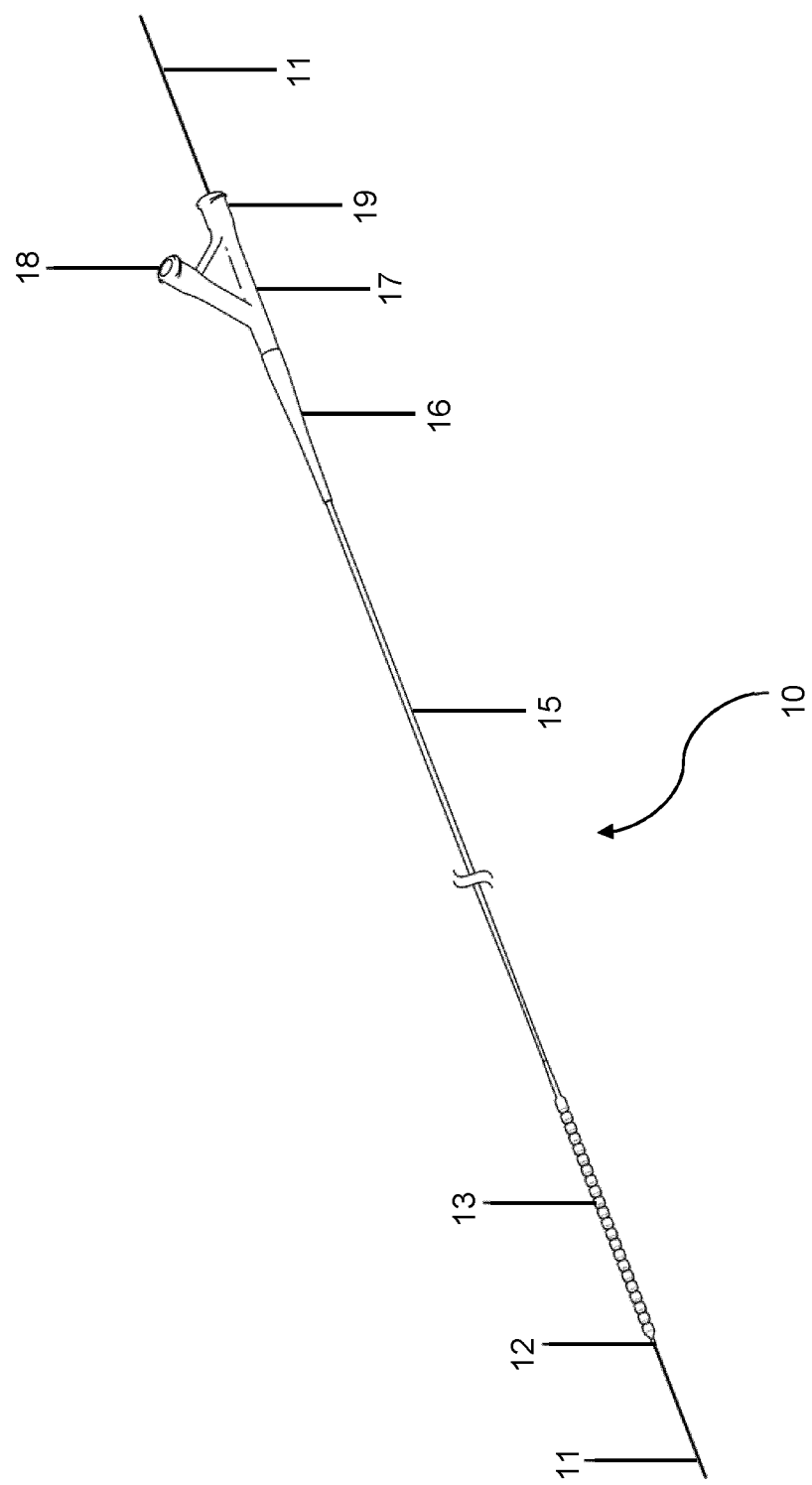
FIG. 1 illustrates a perspective view of an angioplasty balloon catheter in accordance with the present disclosure.

The various components and features of the angioplasty balloon catheter system of the present invention are next described with reference to FIGS. 1 through 11. FIG. 1 illustrates a perspective view of an angioplasty balloon catheter in accordance with the present disclosure. In FIG. 1, the balloon catheter 10 includes, from left to right, a catheter tip 12, an inflatable member or balloon 13, an elongated tubular member or catheter shaft 15, a kink protection sleeve 16, and a manifold 17, that in turn comprises an inflation port 18 and a guide wire port 19. The elongated member 15 extends from the catheter tip 12 or distal end of the catheter to the guide wire port 19 or proximal end of the catheter. The elongated tubular member further 15 includes at least one lumen that is in fluid communication with the inflatable member 13 mounted adjacent to the distal end 12 of the catheter 10. In the implementation shown in FIG. 1 the catheter shaft 15 includes two internal lumens: (1) a first lumen intended as an inflation lumen connected to the inflation port 18; and (2) a second lumen intended as a guide-wire lumen connected to the guide-wire port 19. The angioplasty catheter is shown in an over-the wire configuration, wherein a guidewire 11 extends from an opening at the distal end or tip 12 of the catheter through an opening at the guidewire port 19 at the proximal end.

OTW/RX Configuration

Figure 2:
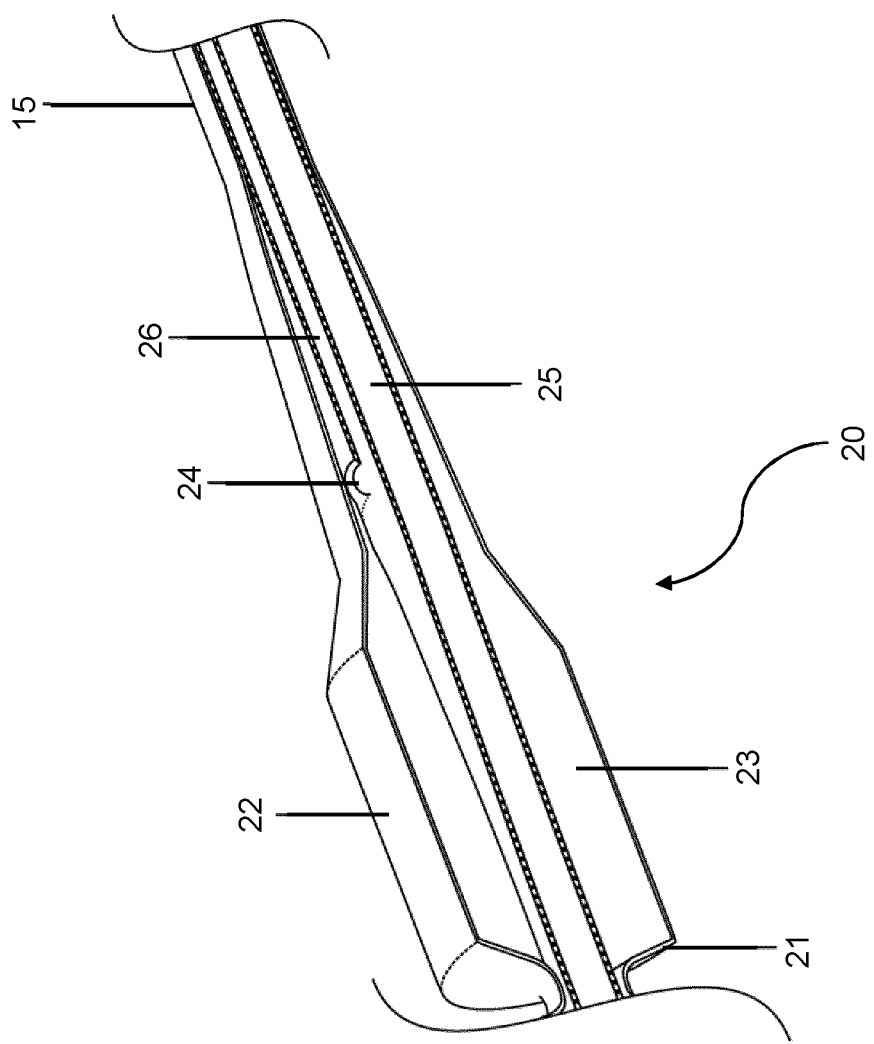
FIG. 2 illustrates a cross-lateral view of a dual-lumen configured inflatable member of an angioplasty balloon catheter of the present disclosure for use in over-the-wire (OTW) configuration.

FIG. 2 illustrates a cross-lateral view of a dual-lumen configured inflatable member of an angioplasty balloon catheter of the present disclosure for use in over-the-wire (OTW) configuration. In FIG. 2, the balloon catheter system 10 of FIG. 1 is shown in an over-the-wire configuration 20, wherein the catheter shaft 15 comprises a dual-lumen consisting of a guide wire lumen 25 and an inflation lumen 26. The guide wire lumen 25 is disposed along the entire length of the catheter 10, and extends from an opening at the catheter tip 12 or distal end through the balloon 13 to an opening at the guide wire port 19 at the proximal end of the catheter. This particular guide-wire lumen configuration enables over-the-wire (OTW) operation of the catheter, meaning that the angioplasty balloon catheter can be slideably mounted onto a guide-wire 11 and translated in either direction along an entire indwelling portion of the guide-wire lumen during insertion of a portion of the catheter shaft into a patient's blood vessel. The OTW configuration therefore may utilize up to the complete usable length of the catheter, which spans from the distal end of the kink-protection sleeve 16 to the distal end or catheter tip 12 of the catheter.

Figure 3:
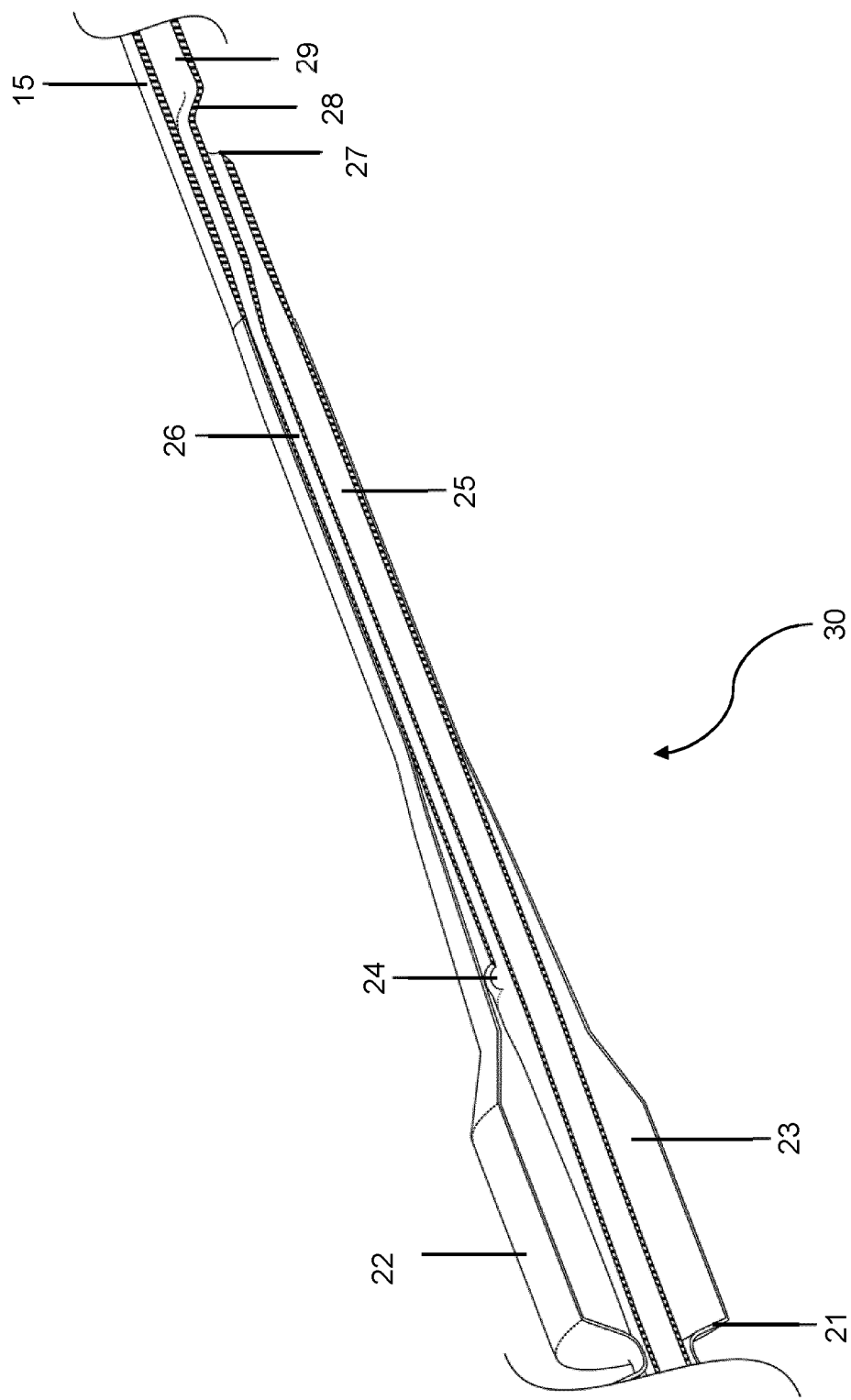
FIG. 3 illustrates a cross-lateral view of a dual-lumen configured inflatable member of an angioplasty balloon catheter of the present disclosure for use in rapid-exchange (RX) configuration.

FIG. 3 illustrates a cross-lateral view of a dual-lumen configured inflatable member of an angioplasty balloon catheter of the present disclosure for use in rapid-exchange (RX) configuration. In FIG. 3, the balloon catheter system 10 of FIG. 1 is shown in a rapid-exchange configuration 30, wherein the catheter shaft 15 comprises a single lumen 29 that distally extends into a dual-lumen portion consisting of a guide wire lumen 25 and an inflation lumen 26. The guide wire lumen 25 extends from an opening at the catheter tip 12 or distal end to a guide wire port 27 located proximal to a most proximal lobe 22 of the balloon 13, and therefore extends at least partially through the elongated member 15. The guide wire port 27 may further include a ramp-like surface 28 to aid in guiding a guidewire 11 through the opening 27. In comparison to the previously shown OTW configurations of FIG. 1 and FIG. 2, the RX configuration 30 of FIG. 3 does not require that an additional guidewire port 19 is present at manifold 17. Thereby, the guide-wire lumen configuration enables rapid-exchange (RX) operation of the catheter 10, meaning that the balloon catheter can be slideably mounted onto a guide-wire 11 and translated in either direction such that the guidewire passes along a portion of the guide-wire lumen 25 during insertion of a portion of the shaft into a patient's blood vessel. The RX configuration 30 therefore may utilize a shorter usable length of the catheter, which spans from the distal end of the guide wire port 27 to the distal end or catheter tip 12 of the catheter. As a result, the RX configuration enables using guidewires of considerably smaller length in comparison to the OTW configuration. In RX operation, the guide-wire 11 is partially exposed alongside the catheter shaft, when located within an indwelling portion, whereas in OTW operation, the guide-wire 11 is fully shielded by the catheter shaft, when located within the indwelling portion.

Shown both in FIG. 2 and FIG. 3, the inflation lumen 26 extends from the inflation port 18 adjacent to the proximal end of the catheter 10 to an opening 24 connected to an interior space or lumen 23 of a first lobe 22 of the balloon 13. The interior lumen 23 of the first lobe 22 of the balloon 13 in turn is shown fluidly connected to one or more adjacent lobes via one or more waist portions 21. Thereby, therapeutic and diagnostic liquids as well as gases, including contrast-agent and saline formulations, drug-formulations, air, and other such liquids and/or gases, may be transferred, under positive pressure inside the inflation lumen or at the inflation port, respectively, from the inflation port 18 through the inflation lumen 26 to one or more lobes 22 of the inflatable member 13, resulting in an inflation of the catheter balloon. The various liquids and/or gases are transferred, under negative pressure inside the inflation lumen 26 or at the inflation port, respectively, from the inflated balloon 13 back through the inflation lumen and out through the inflation port 18, deflating the catheter balloon. "Positive pressure" and "negative pressure" designate pressures which are larger than, or smaller than, respectively, the pressure around balloon 13.

Inflatable Member Configuration

Figure 4:
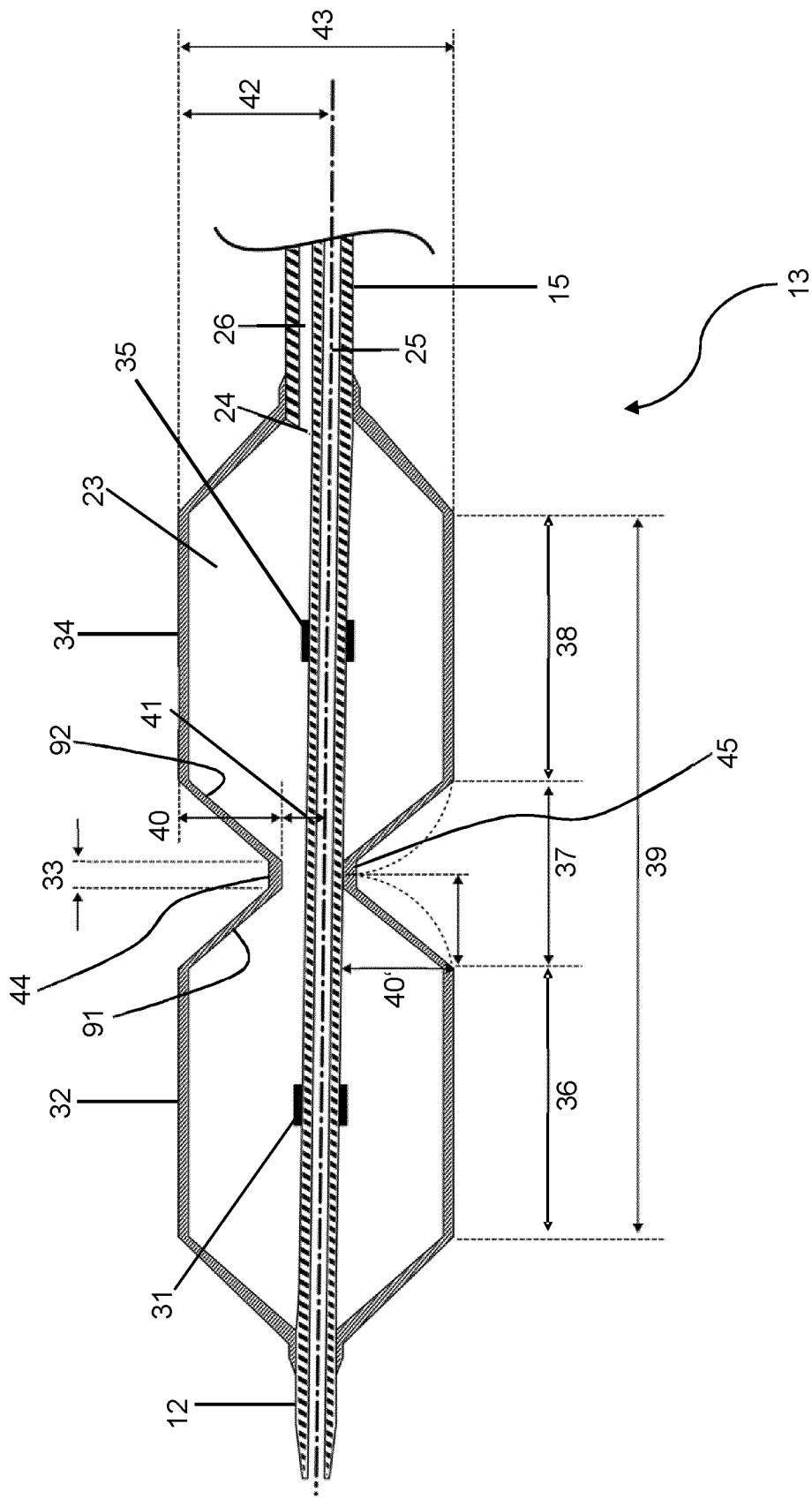

FIGS. 4-10 illustrate cross-sectional views of an inflatable member of the angioplasty balloon catheter in accordance with the present disclosure. In FIG. 4, an inflatable member 13 is shown partially affixed to a catheter shaft 15 of the angioplasty balloon catheter 10. The inflatable member 13 is formed from at least two lobes 32, 34, spaced apart by one or more waist portions 44, 45. The waist portion 44 has a lower base length 33 and an upper base length 37, and two legs 91, 92. In turn, a (mantle) length 39 of the inflatable member 13 is provided through the sum of the individual lengths 36, and 38 of the at least two lobes 32, 34, and the individual length 37 (L) of the one or more waist portions 44, 45, respectively. Further, the upper base of the waist portion 44 of the inflatable member 13 exhibits a first, radial distance or depth 40 relative to the lower base of the waist portion 44, and the lower base of the inflatable member 13 exhibits a second, radial distance or depth 41 relative to a rotational axis (indicated as a dash-dotted line) of the inflatable member 13. Consequently, the sum of the first and second distances, or depths 40, 41 of the waist portion 44 yield an outer radius 42 (R) of the inflatable member 13. The one or more waist portions 44 of the at least two or more lobes 32, 34 of the inflatable member 13 can exhibit one or more length 37 (L) that is adapted to a specific intended use or clinical indication, in particular including the controlled, and sequential cracking of a lesion, and/or the intramural delivery of drugs. In the case of drug delivery applications, the one or more length 37 (L) of the one or more waist portion 44, 45 of the at least two or more lobes 32, 34 of the inflatable member 13 can preferably be adapted to a length aspect of the lesion, and the length selected from at least a set of ranges that includes 0-240 mm, 5-10 mm, 10-30 mm, 30-60 mm, 60-90 mm, 90-120 mm, 120-150 mm, 150-180 mm, 180-210 mm, and 210-240 mm. In the case of controlled lesion cracking, the one or more length 37 (L) of the one or more waist portion 44, 45 of the at least two or more lobes 32, 34 of the inflatable member 13 can preferably be adapted to a diameter aspect of the lesion, and the length selected from at least a set of ranges that includes 0-20 mm, 1-2 mm, 2-4 mm, 4-6 mm, 6-8 mm, 8-10 mm, 10-12 mm, 12-14 mm, 14-16 mm, 16-18 mm, and 18-20 mm. Because the angioplasty catheter of the current disclosure is directed to the combined intended uses of drug delivery and controlled lesion cracking, a combination of both of the above sets of ranges can be desired, and thus, the one or more waist portions 44 of the at least two or more lobes 32, 34 of the inflatable member 13 can exhibit one or more length 37 (L) selected from the above two sets of ranges that are each adapted to a length and diameter aspect of the lesion. Of the above two sets of length ranges, the smaller, diameter-aspected length range constitutes the preferred range. Therefore, as a specific feature of the inflatable member of the present disclosure, the waist portion 44 can preferably exhibit a length 37 (L) not greater than two times the radius 42 (R) of the inflatable member. The upper base length 37 of the waist portion 44, 45 therefore can be designed to not dimensionally exceed an outer diameter 43 of the inflatable member in a pressurized state. Specific technical effects of the segmentation of the inflatable member into the at least two or more lobes via one or more waist portions will be further described in reference to FIGS. 12-20.

In the above provided example, the distal and proximal end of the inflatable member 13 are each affixed to a portion of the catheter shaft 15 to form a fluid-tight space or interior lumen 23 between the inner surface of the inflatable member and the outer surface of the catheter shaft. In reference to the description of FIGS. 2-3, an inflation lumen 26 extends from the inflation port 18 adjacent to the proximal end of the catheter 10 to an opening 24 that is connected to the interior lumen 23 of the first, or most proximal of the at least two lobes 32, 34 of the inflatable member 13. Because in this implementation the waist portion 44 is not adhered to the catheter shaft 15, as opposed to the waist portion 45, the interior lumen 23 of the inflatable member 13 in turn fluidly connects to the one or more adjacent lobes 32 via the one or more waist portions 44. In alternate implementations, one waist portion 45, or more waist portions 44, 45 can be provided not attached to the wall of the catheter shaft 15 to fluidly connect between the one or more lobes 32, 34. Therefore, the one or more waist portion 44, 45 of the inflatable member 13 of the balloon catheter 10 is one or more of: attached, partially attached and not attached to the elongated member 15.

For enabling angiographic visibility, radiopaque markers 31, 35 are attached to the catheter shaft 15 at shaft locations that indicate a lobe position, and/or demarcate the proximal and distal ends or mantle surface of the inflatable member 13. In reference to FIG. 1, the inflatable member 13 of the present disclosure may include a plurality of lobes, for example the inflatable member or balloon may have 2 to 20, 2 to 15, 2 to 10, 3 to 8, 4 to 6 and 2 to 4 lobes. Further, the number of lobes can be selected from an odd or even number. The actual number of lobes can be governed, among others, from a set of balloon lengths and diameters suitable and effective for treating complex lesions.

Generally, in an unpressurized state, the at least two lobes 32, 34 of the inflatable member 13 are provided each folded and pleated, such that subsequent pressurization of the inflatable member individually unfolds each of the two or more lobes. Preferably a number of pleats of the at least two lobes 32, 34 of the folded and pleated inflatable member 13 in an unpressurized state is an uneven number equal or greater than three.

Further, a flap length of the at least two lobes 32, 34 of the folded and pleated inflatable member 13 is preferably selected from at least a range of lengths from about a ratio between 0.25 to 0.75, and more preferably, from a ratio of 0.5 to 0.66 of the radius 42 of the inflatable member, wherein the maximum flap length of the inflatable member is determined by the first depth 40 of the waist portion 44,45, thereby reducing a torsional load that is transferred between the inflatable member and an area to be treated (65, 66). The second depth 41 relative to a rotational axis of the at least two lobes 32, 34 of the folded and pleated inflatable member 13 is preferably selected from a remainder of the above ratio, that is preferably 0.25 (1-0.75) to 0.75 (1-0.25), and more preferably 0.34 (1-0.66) to 0.5 (1-0.5) of the radius 42 of the inflatable member. Further, the second depth 41 is preferably not exceeding a ratio greater than 0.5 relative to a nominal diameter 43 of the inflatable member in a pressurized state. In additional implementations, at least one of the number of pleats and one of the flap length of the at least two lobes 32, 34 of the folded and pleated inflatable member 13 in an unpressurized state are varied.

Preferably, a length 39 of the inflatable member 13 is selected from at least a set of ranges that includes 0-240 mm, 5-10 mm, 10-30 mm, 30-60 mm, 60-90 mm, 90-120 mm, 120-150 mm, 150-180 mm, 180-210 mm, and 210-240 mm. In addition, a length 36, 38 of the at least two lobes 32, 34 of the inflatable member 13 is selected from at least a set of ranges that includes 0-240 mm, 1-5 mm, 5-10 mm, 10-30 mm, 30-60 mm, 60-90 mm, 90-120 mm, 120-150 mm, 150-180 mm, 180-210 mm, and 210-240 mm. Further, the length 36, 38 of the at least two lobes 32, 34 of the inflatable member 13 can include multiple, different lengths.

Preferably, a diameter 43 of the at least two lobes 32, 34 of the inflatable member 13 is selected from at least a set of ranges that includes 0-20 mm, 1-2 mm, 2-4 mm, 4-6 mm, 6-8 mm, 8-10 mm, 10-12 mm, 12-14 mm, 14-16 mm, 16-18 mm, and 18-20 mm. In addition, a diameter 43 of the at least two lobes 32, 34 of the inflatable member can include multiple, different diameters.

Based on the foregoing, at least one of the length and one of the diameter of the at least two lobes 32, 34 can be varied.

Further, the inflatable member 13 of the balloon catheter 10 can comprise a distal predilatation portion and a proximal dilatation portion. In the above, the predilatation portion can consist of at least four lobes, each length 36, 38 selected from a range of not greater than 1-10 mm, preferably 1-5 mm; and each diameter 43 in an unpressurized state selected from a range of not greater than 0.5-2 mm, preferably 1-2 mm; and the dilation portion can consist of at least four lobes, each length 36, 38 selected from a range of greater than 1-10 mm, preferably 1-5 mm; and each diameter 43 in a pressurized state selected from a range of greater than 0.5-2 mm, preferably 1-2 mm.

In additional implementations, the lengths 36, 38 and radii 41, 42, or diameters 43 of the at least two or more lobes, and the lengths 37 and depths 40, 41 of the one or more waist portions can be selected from the same, similar or different, lengths, radii, or depths, and either lobes and/or waist portions can be spaced at equal, similar or different distances from one another, depending on their specific use.

In the provided examples of FIGS. 1-4, the dual lumens of the inflatable member 13 are arranged in a side by side (or parallel) configuration. In alternate implementations, more than two lumens can be present, and the lumens provided in parallel and/or co-axial arrangement, as well as combinations selected therefrom. Such examples will be shown in FIGS. 5-7.

Figure 5:
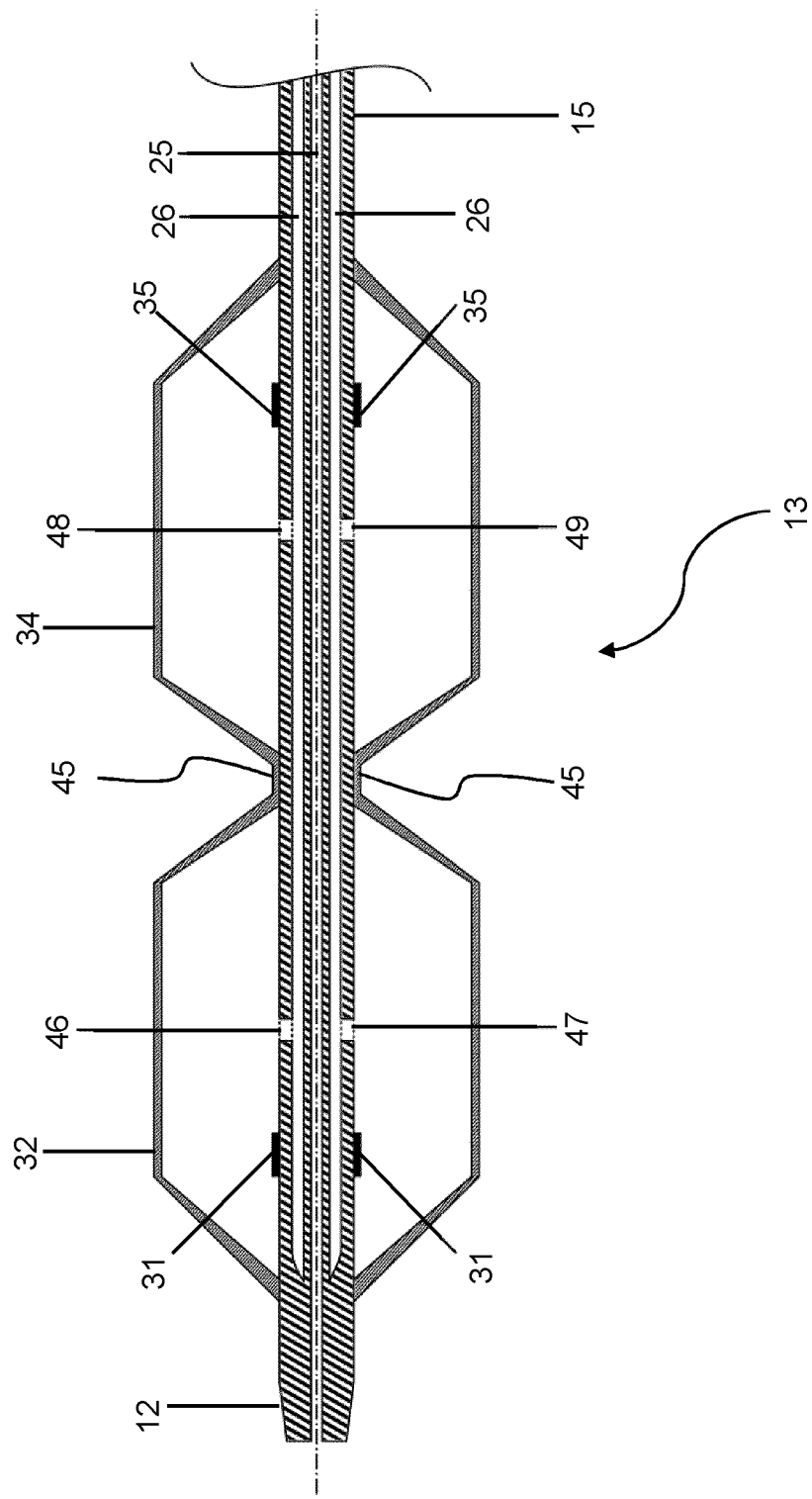

For further illustration, FIG. 5 shows an implementation of the inflatable member 13 with a coaxial dual-lumen configuration. FIG. 5 differs from the previous dual-lumen configuration shown in FIG. 4, in that the inflation lumen 26 of the catheter shaft 15 is coaxially formed around the guide wire lumen 25, and extends distally beyond the proximal end of the inflatable member 13 to its distal end or tip 12. Further, one or more waist portion 45 of the at least two or more lobes 32, 34 is attached to the wall of the catheter shaft 15, and additional openings 48, 49 situated in the first, or most proximal lobe 34, and additional openings 46, 47 situated in the second or most distal lobe 32 individually extend the inflation lumen 26 into each fluid-tight space present between the inner surface of each lobe and outer surface of the catheter shaft. Thereby, the inflatable member 13 including the at least two lobes 32, 34 is in fluid communication with the inflation port 18 via the inflation lumen 26. The coaxial dual-lumen configuration of FIG. 5 can be particularly advantageous over a parallel arrangement, when an individual inflation/deflation of each lobe is desired, or when additional lumens for separately administering therapeutic and diagnostic liquids are needed.

Figure 6:
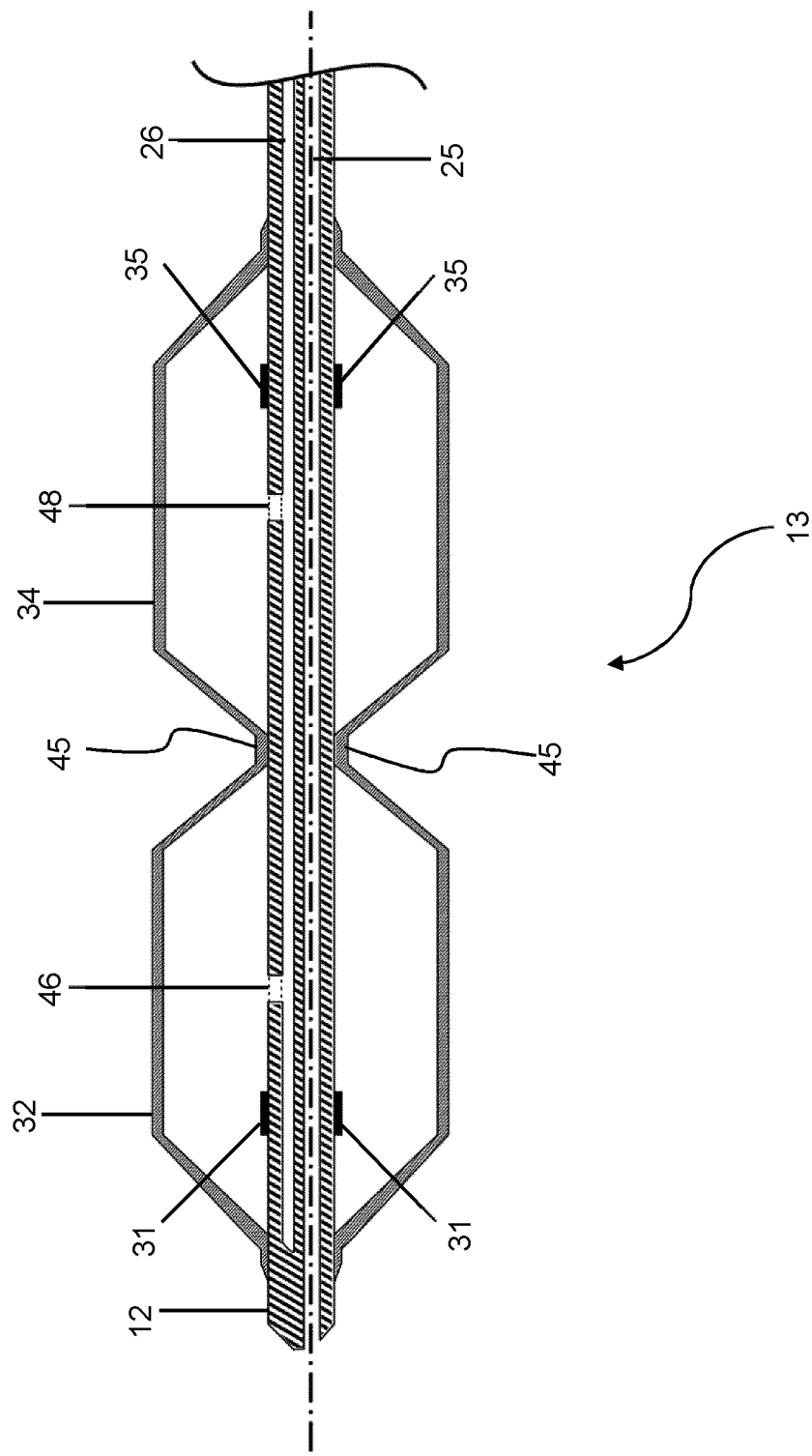

For comparative purposes, FIG. 6 illustrates an alternative implementation of a parallel dual-lumen configuration that is similar to the dual-lumen configuration shown in FIG. 4. However, the dual-lumen configuration differs in that the inflation lumen 26 extends distally beyond the proximal end of the inflatable member 13 to the distal end or catheter tip 12, and one or more waist portion 45 of the at least two or more lobes 32, 34 is attached to the wall of the catheter shaft 15. The catheter shaft further includes at least two openings 46, 48 that individually extend from the inflation lumen 26 through the wall of the catheter shaft 15 into each fluid-tight space present between the inner surface of each lobe 32, 34 and the outer surface of the catheter shaft. Thereby, the inflatable member 13 including the at least two lobes 32, 34 is in fluid communication with the inflation port 18 via the inflation lumen 26. The parallel dual-lumen configuration of FIG. 6 can be particularly advantageous over the dual-lumen configuration shown in FIG. 4, when an individual inflation/ deflation of each lobe is desired, or when an increased stiffness of the inflatable member 13 is needed.

Figure 7:
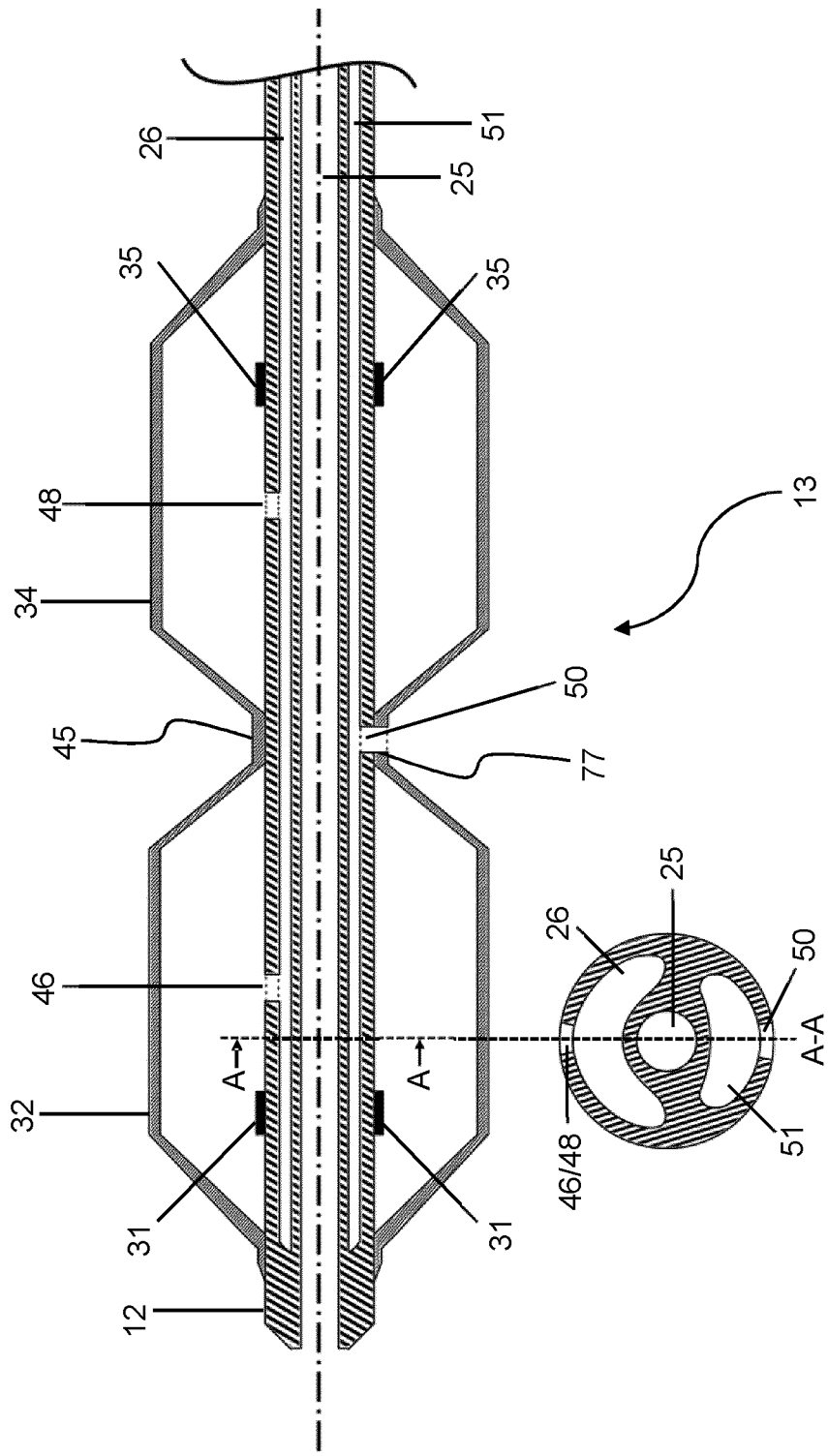

FIG. 7 provides an alternative implementation of a coaxial triple-lumen configuration that is similar to the coaxial dual-lumen configuration shown in FIG. 5. In FIG. 7, however, the triple lumen configuration comprises a central guide wire lumen 25, an inflation lumen 26, and an additional drug perfusion lumen 51, wherein the inflation and drug perfusion lumen are separate lumens that are not in fluid communication with each other, and coaxially formed around the guide wire lumen. An additional insert beneath lobe 32 shows a vertical, dashed line at a position 'A' along a length of the elongated member 15, and a corresponding vertical cross-section 'A-A' that further illustrates the coaxial triple-lumen configuration. As evidenced from the horizontal and vertical cross-sections, the drug perfusion lumen 51 extends from a drug perfusion port located at the manifold 17 (not shown) into a drug release opening 50 located in the waist portion 77 of the at least two lobes 32, 34 of the inflatable member 13. Thereby, the triple lumen configuration enables the inflation/deflation of the at least two lobes 32, 34 and the perfusion of therapeutic and diagnostic liquids, or agents, into the waist portion 45/77 at substantially the same, similar or different stages of the treatment procedure. For example, prior to administering treatment to a desired target area, the lobes 32, 34 of the inflatable member 13 can be inflated to prevent blood flow through the target area, so as to prevent the inadvertent release of therapeutic liquids into the blood stream of the patient, followed by the targeted delivery of therapeutic liquids into the waist portion 45/77 that is located in the target treatment area. After a desired therapeutic treatment time window has elapsed, residual therapeutic agents can be withdrawn into the drug perfusion lumen 51, and the lobes 32, 34 of the inflatable member 13 deflated to restore blood flow to the target treatment area. In the implementation of FIG. 7, the waist portions 45, 77 are shown adhered to the catheter shaft 15, however, the waist portions can also be provided non-adhered (44, 77), adhered (45), or partially adhered to the shaft (44,45), as exemplarily illustrated in FIG. 4. In an alternate implementation, the inflation lumen 26 can simultaneously be a drug perfusion lumen, and the inflation port 18 can simultaneously be a drug perfusion port. In additional implementations, individual coaxial lumens can be adhered, partially adhered or non-adhered to each other along a length of the lumen. Such means may serve to reinforce or stabilize a position of one or more of the coaxial lumens with respect to the elongated member. For example, the coaxial lumen configuration can include stabilization welds, preferably along a proximal lumen portion of the elongated member. In addition, the various openings and ports at the elongated member and/or waist portion used for exchanging guidewires, and for transferring of therapeutic and diagnostic liquids, and/or gases can be provided structurally reinforced.

Summarizing the aforementioned constructional aspects and features of the balloon catheter in accordance to the present disclosure, the balloon catheter 10 at least comprises:
- an elongated member 15 having a proximal end 19, a distal end 12, and at least one lumen 25, 26 extending at least partially through the elongated member; and
- an inflatable member 13 affixed to the elongated member adjacent to the distal end and in fluid communication with the at least one lumen 26, the inflatable member having a radius R (42) and including at least two lobes 32, 34, the at least two lobes separated from each other by one or more waist portion 44, 45;
- wherein in an unpressurized state, the at least two lobes 32, 34 of the inflatable member 13 are provided each folded and pleated, such that subsequent pressurization of the inflatable member individually unfolds each of the two or more lobes.

Further, the balloon catheter 10 comprises:
a catheter tip 12;
a kink-protection sleeve 16; and
a manifold 19.

In addition, the manifold 19 of the balloon catheter 10 comprises:
- an inflation port 18; and
- a guide-wire port 19, 27-28.

Further, the elongated member 15 of the balloon catheter 10 comprises:
- an inflation lumen 26, and
- a guide-wire lumen 25, the guidewire lumen extending at least partially through the elongated member (27).

In the above, the guide wire lumen 25 of the elongated member 15 of the balloon catheter 10 connects the catheter tip 12 to the guide-wire port 19, 28, and the inflation lumen 26 is in fluid communication with the inflatable member 13.

In one implementation, the inflation lumen 26 simultaneously is a drug perfusion lumen, and the inflation port 18 simultaneously is a drug perfusion port.

Based on the foregoing, the elongated member 15 of the balloon catheter 10 is configured as a dual-lumen shaft and a dual-lumen configuration of the elongated member is selected from a group consisting of a parallel arrangement, a coaxial arrangement and a combination of coaxial and parallel arrangements.

In an alternate implementation, the manifold 19 of the balloon catheter 10 further comprises a drug perfusion port, and the elongated member 15 further comprises a drug perfusion lumen 51. In the alternate and the preceding implementation, the one or more waist portion 77 of the inflatable member 13 comprises at least one drug release opening 50, wherein the at least one drug release opening 50 is in fluid communication with a drug perfusion lumen 26, 51 within the elongated member 15.

In the alternate implementation, the elongated member 15 is configured as a triple-lumen shaft and a triple-lumen configuration of the elongated member is selected from a group consisting of a parallel arrangement, a coaxial arrangement and a combination of coaxial and parallel arrangements.

Structural Reinforcement Elements

Figure 8:
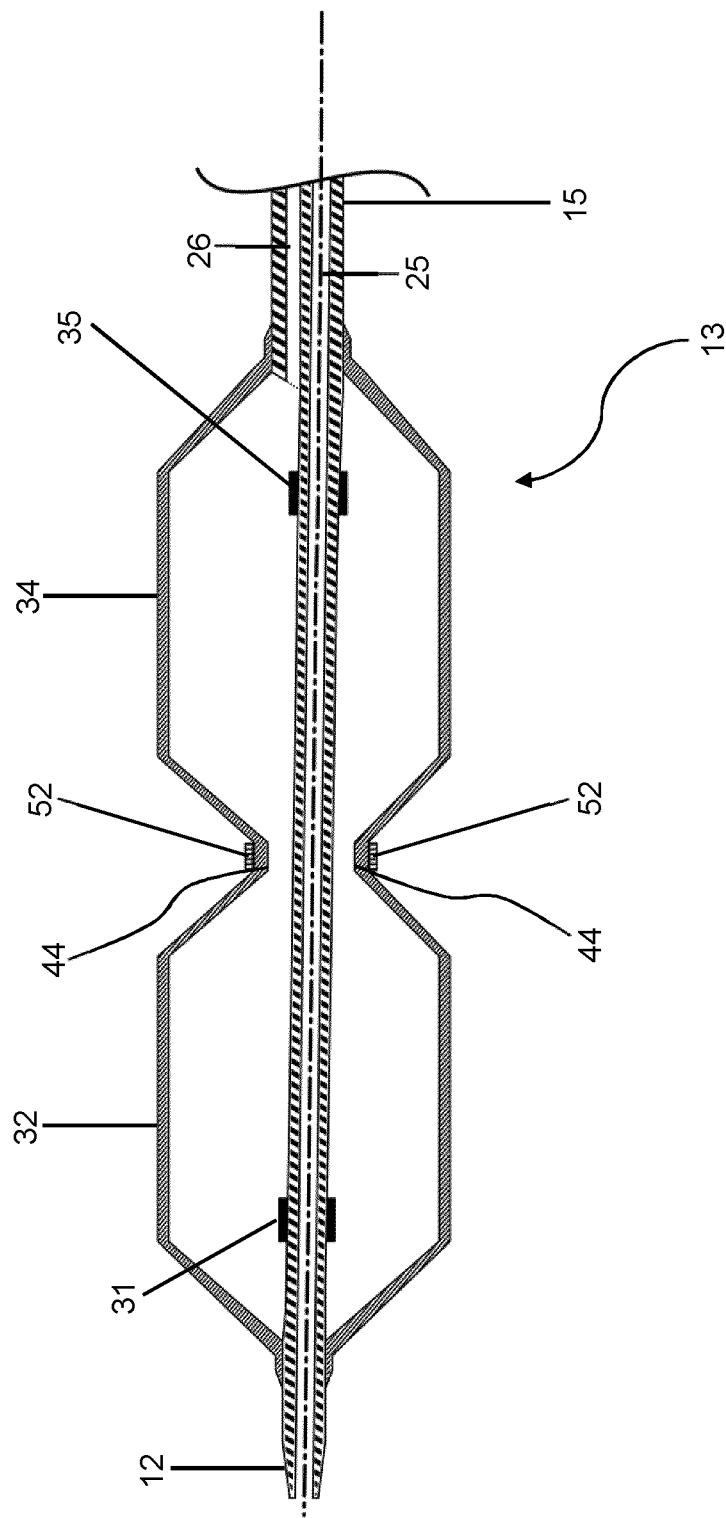

FIGS. 8-10 provide additional alternative implementations of the inflatable member 13 in accordance to the present disclosure. In FIG. 8, the inflatable member 13 is based on the dual-lumen configuration shown previously in FIG. 4, and includes at least two or more lobes 32, 34 and one or more waist portions 44, 45. However, in comparison to FIG. 4, the one or more waist portions 44, 45 are not partially or fully adhered to the catheter shaft 15, and include one or more additional structural element 52 that is disposed within the waist portions 44, 45, respectively. In reference to FIG. 4, the one or more structural element 52 is configured to retain the lower base(s) of the one or more waist portions 44, 45, such that when the inflatable member 13 is pressurized, the waist portions 44, 45 are retained at a pre-determined depth 41 relative to a rotational axis of the inflatable member 13. The depth of the lower base is defined by a diameter of the structural element 52, whereas the at least two lobes 32, 34 of the inflatable member are free to expand to a diameter 43, as exemplarily referenced in FIG. 4. The one or more structural element 52 thereby reinforces at least one or more lower base(s) of the one or more waist portions 44, 45, and aids in stabilizing the inflatable member 13 such, that when the inflatable member 13 is pressurized, the axial stability or compliance of the inflatable member is further improved, particularly in the case when the one or more waist portions 44, 45 are not adhered to the catheter shaft 15. In this example, the one or more structural element 52 therefore aids in securing a waist portion to an inflatable member 13 and/or the catheter shaft 15. Additional reinforcement of the one or more lower base(s) of the one or more waist portions 44, 45 through attachment to the catheter shaft 15, or provision of additional one or more structural element(s) 52 disposed in the one or more waist portions 44, 45 of the inflatable member 13 can be particularly advantageous when an additional axial and radial stabilization or compliance of the inflatable member is desired, or radial expansion of the waist portion needs to be suppressed.

In further implementations, the one or more structural member 52 can be provided fixedly attached to an outer surface of the inflatable member 13 or disposed between multiple layers that in turn form a wall or outer surface of the inflatable member 13. It is also contemplated that the structural member 52 can be provided not fixedly attached to the inflatable member, instead the structural member 52 is disposed within the waist portion 44, 45, wherein a geometrical shape of the inflatable member fixates the position of the structural member 52 within the waist portions 44, 45. The structural element 52 that serves as a means for reinforcement of the at least one of the one or more waist portions is selected from a group consisting of a fiber, a seam, a thread, a ring, a tubing, an adhesive, a crosslinked polymer, a point-like, a line-like, a helical, a circular, a cylindrical, a semi-circular, an arced, layered or interwoven attachment to the elongated member and combinations formed therefrom. Further, the structural element 52 can be provided in the form of a rigid, ductile, elastic, and/or spring-like material, and the material additionally be provided in the form of a solid, semi-solid, mesh-like or porous material, and/or suitable combinations selected therefrom. Materials preferably suitable for use as a structural element include those constructed of a material having a mechanical strength equal to or higher than that of the material(s) of which the inflatable member is formed from, for example the structural element may be constructed of a thermoplastic or thermoset polymer, a non-crosslinked or crosslinked polymer, an adhesive, ceramics, radiopaque materials and material compositions, and metals including stainless steel, nitinol, cobalt chromium or the same or similar biocompatible materials. In one preferred example, the structural element is made of the same material the balloon is formed from. In this case, the structural element can be either integrally formed with the balloon during the manufacture of the balloon or the structural element may be directly attached to the balloon using adhesive attachment mechanisms, chemical attachment mechanisms or other physical attachment processes such as laser welding, ultrasound welding, friction welding, plasma welding, thermal bonding, thermal forming or any suitable combination formed therefrom. In another example of the present disclosure, the structural element 30 is integrally formed by photo-crosslinking of the balloon material at the desired location(s) of the structural element(s) 52. In a further example, the balloon is formed of a multilayer material and the structural element 52 is disposed between several layers of the balloon during manufacture. Preferably, the structural element 52 is a cylindrical portion of a heat-shrinkable tubing material which is placed over the balloon body and heat treated until mechanical and/or dimensional stability is reached. In general, the structural element 52 is one of a fiber, a seam, a thread, a ring, a tubing, an adhesive, a polymer, a point-like, a line-like, a helical, a circular, a cylindrical, a semi-circular, an arced, layered or interwoven attachment, preferably with a constant width and thickness. Preferably, the structural element has a varying width over its circumference, in other words, the structural element is asymmetric.

For further illustration, FIGS. 9-10 provide several alternative implementations of an inflatable member in accordance to the present disclosure. In these examples, the inflatable member 13 further comprises one or more structural elements disposed in the one or more waist portions of the at least two or more lobes. In FIG. 9, the inflatable member comprises a series of six lobes 53, 54, 55, 56, 57 and 58, that are equidistantly spaced apart by a series of five waist portions, each reinforced with an asymmetric structural element 59. The structural elements of this example are formed from a series of shrink tubing, each cut to an isosceles trapezoid form. These asymmetric shrink tubing pieces are then placed over each waist portion of the inflatable member 13, and heat-shrunk to form an inflatable member in accordance to the present disclosure, as shown. In this example, the asymmetric structural elements are arranged in the same orientation along the length of the inflatable member. Thereby, upon pressurization, the unidirectional orientation and arrangement of the asymmetric structured elements leads to a continuously curved shape of the inflatable member that facilitates enhanced bending modes, if so desired. It is further contemplated, that the above example is not limited to the exact disposition of the structural element, for example, instead of shrink tubing any other of the aforementioned structural elements can be equivalently implemented in an asymmetric form.

In comparison, FIG. 10 illustrates an inflatable member comprising a series of four lobes 53, 54, 55, and 56 that are equidistantly spaced apart by a series of three waist portions, each reinforced with an asymmetric structural element 60. In FIG. 10, however, the asymmetric structural elements 60 are alternatingly arranged, reversing their orientation every other element along the length of the inflatable member. Thereby, upon pressurization, the bi-directional orientation of the asymmetric structural elements leads to a meandering/undulating shape of the inflatable member that facilitates enhanced bending modes, if so desired. Alternative implementations include placing asymmetric structural elements in a spiraling or helical orientation along the length of the inflatable member, or other specific arrangements and orientations that in turn facilitate other suitable bending modes of the inflatable member, as desired for a specific use. Such reinforced inflatable members of the present disclosure can be suitable for facilitating an enhanced adaption of the inflated balloon portion to the natural vessel anatomy, and may further prevent undesired straightening and distension of a diseased vessel portion.

By providing an inflatable member in accordance to the present disclosure, additional bending modes of the inflatable member are enabled, that further enhance 3D plaque modulation of a lesion. Thereby, the angioplasty balloon catheter can suitably exhibit an even more enhanced, directional capability to controllably inflate in the obstructed or diseased vessel portion, wherein the application of focalized pressure to the lesion results in a controllable fracture of the lesion at preferably multiple locations, which in turn facilitates an efficient and selective modulation, modification, and/or fracture of target lesions at substantially lower pressure ranges compared to conventional angioplasty catheters. As a result, trauma can be reduced and a safe and clinically more effective treatment of the patient can be performed.

Summarizing the above constructional aspects and features of the balloon catheter 10 in accordance to the present disclosure, the one or more waist portion 44, 45 of the balloon catheter 10 can include one or more structural element 52. In turn, the one or more structural element 52 reinforces at least one or more of the one or more waist portions 44, 45. In the various implementations, the one or more structural element 52 of the balloon catheter 10 serves as a means for reinforcement of at least one of the one or more waist portions 44, 45 and is selected from a group consisting of a fiber, a seam, a thread, a ring, a tubing, an adhesive, a crosslinked polymer, a point-like, a line-like, a helical, a circular, a cylindrical, a semi-circular, an arced, a layered, and a interwoven attachment to the elongated member and combinations formed therefrom. Further, the one or more structural element 52 of the balloon catheter 10 is preferably asymmetric, and can be arranged in a unidirectional orientation relative to a length axis of the inflatable member 13, in a bidirectional orientation relative to a length axis of the inflatable member 13 and/or arranged in an alternating combination of unidirectional and bidirectional orientation relative to a length axis of the inflatable member 13.

Manufacturing Aspects

Concerning the general construction aspects of the angioplasty catheter system of the present disclosure, the catheter components can be manufactured from biocompatible, polymeric, metallic and ceramic materials. For example, the catheter components, including the inflatable member, can be manufactured from aliphatic, semi-aromatic and aromatic polyamides (PA); polyether ether ketones (PEEK); polyethers; polyimides (PI); linear and nonlinear, branched or non-branched, low molecular weight, medium molecular weight, or high molecular weight; low density, medium density, or high density polyolefins, including polyethylene (PE, LD-PE, HD-PE) and polypropylene (PP), silicones, thermoplastic elastomers, such as polyurethanes (TPEs) and fluoroelastomers, for example FEP or PTFE, polycarbonates (PC), polyesters such as polyethylene terephthalate (PET) and combinations, including blends and copolymers of any of these materials, such as polyether block amides (PEBA), for example.

Further, the catheter components, including the inflatable member, can be fabricated in a single layer, dual-layer, or in multi-layer configuration. In the instance of dual-layer or multi-layer configurations, certain catheter elements, including for example the shaft or the inflatable member, may utilize the same material for each layer or may utilize different materials for each layer. The multiple layers may be glued, melted or fused together with or without an adhesive, or by employing a co-extrusion or welding process. Alternatively, the multiple layers are not required to be attached, glued or welded together; instead, the multiple layers may be allowed to move independently. Additionally, the elastic modulus, durometer or hardness of the materials selected for each layer or component of the catheter system can be varied to beneficially alter the performance aspects of the individual catheter components.

In addition, the chemical functionality and/or physical polarity of the catheter materials can be changed to enhance interfacial adhesion between the differing layers and/or to provide surfaces and/or inner lumen with an increased lubriciousness or changed surface energy when in contact with guide wires, therapeutic and diagnostic liquids, or functional coatings, for example. These chemical and physical treatments or alternations may include for instance chemical additives that can introduce another chemical functionality to the interfacial surface, when added to an exemplary base polymer formulation intended to form one or more layers of the catheter component, for example, including functional groups such as carboxy- and/or amino groups, which can effectively enhance the underlying polarity of the layer and the substrate, thus facilitating enhanced adhesion and mechanical fixation strength in between one or more layered structures of catheter components.

Other surface modifications, such as coatings and/or plasma techniques can be employed for further changing the chemical and/or the mechanical properties of the materials, layers or components of the angioplasty catheter system, wherein the modification of the catheter materials may affect the polarity, surface energy and/or friction coefficient of layers and/or surfaces of the catheter components. Still, other suitable techniques may incorporate additives, adhesives and/or filling agents, which can introduce other beneficial properties to the catheter materials. For example, the components of the catheter system may incorporate radiopaque elements embedded within polymeric materials to selectively increase fluoroscopic visibility at desired locations. Alternatively, or supplementary, the components of the catheter system may incorporate dyes or pigments at select locations to provide visible color-indications to a treatment provider. Additionally, the shaft may incorporate fluoropolymer-based filler particles/fibers to permanently decrease the frictional coefficient as compared to an untreated base-polymer formulation or activatable, single-use coatings. Furthermore, the catheter components, including the shaft and inflatable member can be provided reinforced and may contain metal or polymer-based strands, fibers, wires, braids, meshes and/or fabrics embedded as layers, sections or regions into the base-material.

Concerning the constructional characteristics of the inflatable member, the materials utilized in the construction can be selected, configured and formulated such, that the balloon responds in specific ways to the application of external pressure. By way of construction, the elongated tubular member responds to the application of pressure by two distinct growth mechanisms, namely by a change of axial length and radial diameter. This characteristic change of the balloons' dimensional characteristics during application of pressure is generally referred to as dimensional compliance. Particularly with respect to the target vessel diameter of the treated lesion, the radial compliance, often termed 'balloon compliance' as listed on the product label (or recorded as 'compliance curve'), describes the way of which the diameter of the balloon is going to respond to the application of pressure. The change in axial (longitudinal) dimensions is accordingly referred to as axial compliance. By choice of materials, the dilation elements or balloons can be embodied as compliant balloons, semi-compliant and non-compliant balloons. Compliant medical balloons may expand by 100% or greater upon inflation. Non-compliant dilation balloons expand very little, if at all (<7%), when pressurized from a nominal diameter to a rated burst pressure. Semi-compliant balloons exhibit a moderate degree of expansion (≥7-12%), when pressurized from its nominal or operating pressure (e.g. the pressure at which the balloon reaches its nominal diameter) to its rated burst pressure (e.g. the undesirable pressure threshold at which the balloon can be subject to rupture or burst). Other than by choice of materials and constructional aspects, the desired compliance characteristics of the inflatable member can favorably be controlled through the manufacturing process.

The inflatable members of the present disclosure can be manufactured using known manufacturing methods such as balloon blowing, blow molding, thermoforming, dip molding, or any other manufacturing methods suitable for the manufacture of balloons. It shall be understood to one of ordinary skill in the art that conventional balloon manufacturing techniques can be utilized within the manufacture of balloons of the present disclosure. For example, the materials of the balloon may be subjected to mechanical processes before, during or after the manufacture of the balloon. For instance, when a blowing process is utilized for the manufacturing process, the tubular member from which the balloon is to be formed can be stretched before, during or after the blowing process. Yet still, the temperature as well as the inflation pressure or other parameters can be changed during the manufacturing process to affect the properties of the manufactured balloon.

For further illustration, FIG. 11A and FIG. 11 B provide cross-sectional views of a waist portion of the inflatable member manufactured by balloon blowing and/or thermoforming in accordance with the present disclosure. In FIG. 11A, characteristic wall thickness proportions of an inflatable member manufactured by a single stage balloon blowing process are shown. The inflatable member includes a proximal and a distal end, each having a first wall thickness 61, at least two or more lobes 32, 34, each having a second wall thickness 62, and one or more waist portions 44, each having a third wall thickness 63. In FIG. 11A and FIG. 11 B, the first wall thickness 61 is exemplarily determined as the average of one or more wall thickness at the proximal and distal end (neck/cone) of the inflatable member 13. The second wall thickness 62 is exemplarily determined as the average of one or more (mantle) wall thickness across the lengths 36, and 38 of the at least two lobes 32, 34, and the third wall thickness 63 is determined as the average of one or more wall thickness across the waist portion length 37 of the one or more waist portions 44, 45, respectively. As a result of the single stage balloon blowing process, the first wall thickness 61 exceeds the second wall thickness 62, and the third wall thickness 63 exceeds the second wall thickness 62. Thereby, application of a single stage balloon blowing process results in an inflatable member, wherein the wall thickness 63 at the waist portion 44 is typically higher than the wall thickness 62 of the at least two or more lobes 32, 34 of the inflatable member. This particular single stage manufacturing process can therefore be advantageous for such situations, where a reinforced waist portion with decreased flexibility is desired. The decreased flexibility at the waist portion is particular beneficial in reducing an amount of axial load that is transferred between the inflatable member and an area to be treated 65, 66.

Preferably, however, it can be desired that the inflatable member of the present disclosure exhibits a third wall thickness 63 at the one or more waist portions 44, that does not exceed the second wall thickness 62 at the least two or more lobes 32, 34. The inventors of the current disclosure have found that the above feature can be achieved by combining a balloon blowing process with a consecutive thermoforming process. For further illustration, FIG. 11B provides characteristic wall thickness proportions of an inflatable member manufactured by a two stage process consisting of a first stage balloon blowing and second stage thermoforming process. In FIG. 11B, the inflatable member includes a proximal and a distal end, each having a first wall thickness 61, at least two or more lobes 32, 34, each having a second wall thickness 62, and one or more waist portions 44, each having a third wall thickness 63. As a result of performing a first stage balloon blowing and a second stage thermoforming process, the first wall thickness 61 exceeds the second wall thickness 62, and second wall thickness 62 exceeds the third wall thickness 63. Thereby, application of a two stage process consisting of a first stage balloon blowing and second stage thermoforming process results in an inflatable member, wherein the wall thickness 63 at the waist portion 44 is thinner than the wall thickness 62 of the at least two or more lobes 32, 34 of the inflatable member. This particular two-stage manufacturing process can be advantageous for such situations, where a thinned out waist portion 44 with increased flexibility is desired. The increased flexibility at the waist portion is particular beneficial in enhancing a magnitude of variable directional forces 70, 73 conveyed onto a portion 66 of the area to be treated. These particular effects will further be described in reference to FIGS. 12-13, and FIGS. 17-18.

In additional implementations, a flexibility at the one or more waist portions of the at least two or more lobes can be varied, for example provided as a set of increased and decreased flexibilities, which, when combined, result in a favorable combination of improved axial stability and increase of the magnitude of variable directional forces created at the waist portions.

Summarizing the additional constructional aspects and features of the balloon catheter according to the disclosure, the inflatable member 13 of the balloon catheter 10 further includes:

- a proximal and a distal end, each having a first wall thickness 61;
- at least two lobes 32, 34, each having a second wall thickness 62, and
- one or more waist portions 44, 45, each having a third wall thickness 63.

In one implementation, the first wall thickness 61 of the inflatable member of the balloon catheter 10 exceeds the second wall thickness 62, and the second wall thickness exceeds the third wall thickness 63, thereby increasing flexibility at the one or more waist portion 44, 45, and enhancing a magnitude of variable directional forces 70, 73 conveyed onto a portion 66 of the area to be treated 65.

In another implementation, the first wall thickness 61 of the inflatable member exceeds the second wall thickness 62, and the third wall thickness 63 exceeds the second wall thickness, thereby decreasing flexibility at the one or more waist portion 44,45, and reducing an amount of axial load that is transferred between the inflatable member and an area to be treated (65,66).

The inflatable members shown and described with regard to FIGS. 1-11 have been designed to be utilized to perform angioplasty procedures in accordance to the present disclosure. Unlike conventional angioplasty catheters comprising single-membered angioplasty balloons, the angioplasty catheters of the current disclosure comprise an elongated member having a proximal end, a distal end, and at least one lumen extending at least partially through the elongated member; and an inflatable member proximally affixed to the elongated member adjacent to the distal end and in fluid communication with the at least one lumen, the inflatable member having a radius R and including at least two lobes, the at least two lobes separated from each other by one or more waist portion, wherein in an unpressurized state, the at least two lobes of the inflatable member are provided each folded and pleated, such that subsequent pressurization of the inflatable member individually unfolds each of the two or more lobes. Through provision of an inflatable member according to the criteria set forth above and below, the inflatable members of the present disclosure can provide a novel combination of a concerted radial expansion and simultaneous longitudinal bending mode, that enables delivering focalized pressure to a lesion, and thereby, resulting in a controllable fracture of the lesion at preferably multiple locations. Because the inflatable member of the current disclosure can be utilized at comparatively lower pressures compared to conventional angioplasty balloons, a substantially atraumatic, three dimensional plaque modulation is achieved. For further illustration, the specific technical effects are next described with reference to FIGS. 12-20.

Figure 12:
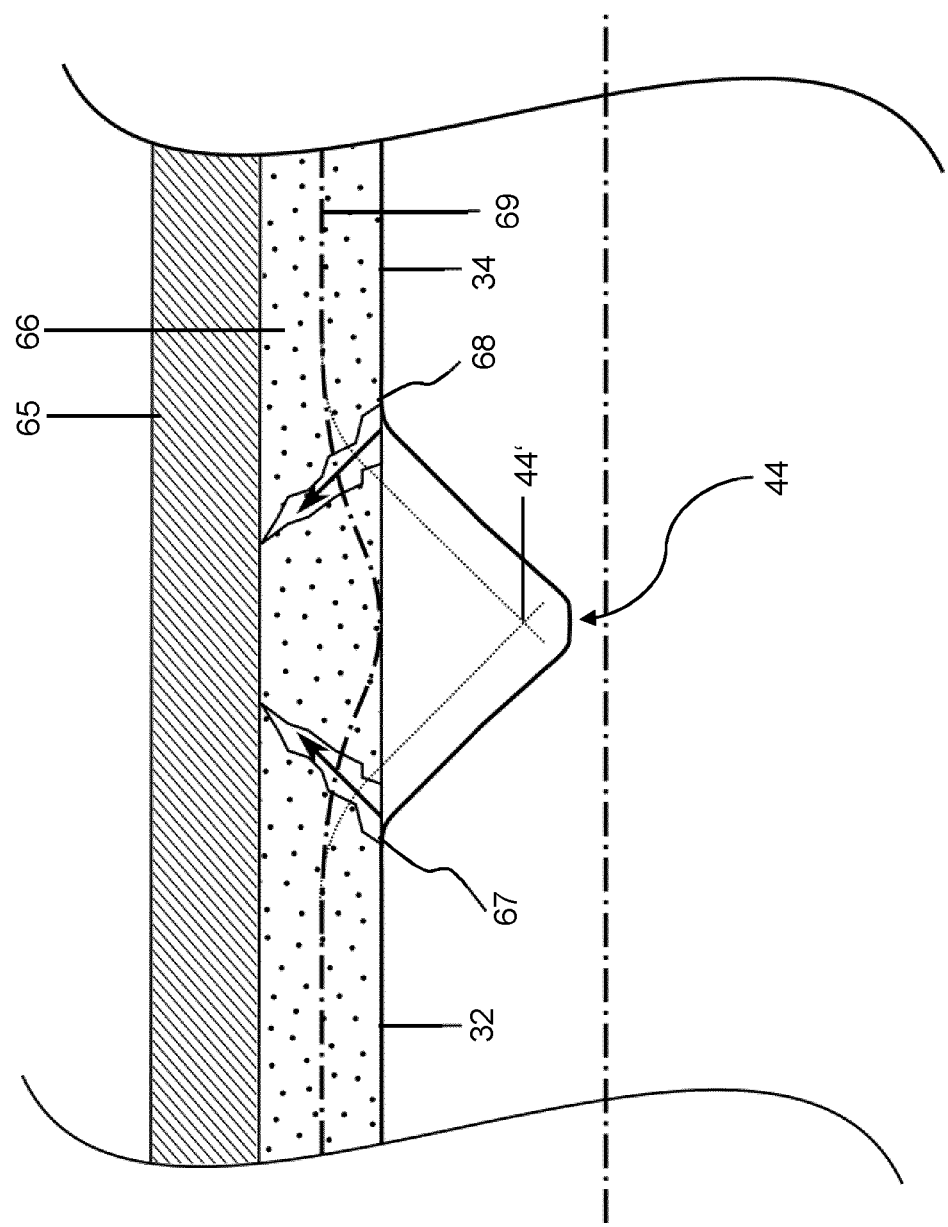
FIG. 12 is a graphical representation of lesion-fracturing effects observed when applying an inflatable member of the present disclosure to a calcified lesion.

FIG. 12 is a graphical representation of lesion-fracturing effects observed when applying an inflatable member of the present disclosure to a calcified lesion. In FIG. 12, an inflatable member comprising at least two lobes 32, 34, and one or more waist portions 44 are depicted. The inflatable member is shown in contact to a lesion 66 that is situated in a blood vessel 65. In reference to FIG. 4, upon pressurization of the inflatable member 13, the position (of the lower base) of the waist portion 44 is shifted to a second position 44' and the inflatable member pushed into the lesion. In the pressurized state, the at least two or more lobes 32, 34 of the inflatable member 13 controllably convey opposing axial and equidirectional radial loads or forces between the lobes and an area to be treated (65, 66), resulting in a specific stress distribution profile that is indicated as a dash-dotted line in FIG. 12. The stress distribution along the mantle surface of the inflatable member changes from a maximum radial stress state directly above the at least two or more lobes 32, 34 to a radial stress relief zone directly above the waist portion 44. As a result, variable directional forces, indicated by black arrows, are created through concerted interaction between the axial and radial force components present at the waist portion. In turn, these directional forces are projected onto a portion 66 of the area to be treated 65 that is situated around the waist portion 44. The directional forces create additional cleavage planes 67, 68 that favorably fracture the lesion 66. In other words, because the variable directional forces conveyed between the lobes and around the waist portion differ from the radial forces conveyed by the lobe portions of the inflatable member and an remainder of the area to be treated, a variable pressure differential is induced between the lobes and waist portion of the inflatable member that, when conveyed to an area to be treated, results in the preferential formation of lesion fractures around the waist portion of the inflatable member. The directional forces are variable in magnitude and direction depending on the pressurization state of the inflatable member. Due to the concerted action of radial expansion, and simultaneous longitudinal bending, focalized pressure is delivered to the lesion, and thereby, results in a controllable fracture of the lesion at multiple locations situated around the waist portion. In other words, a segmentation of the inflatable member at the at least two or more lobes induces a 'pressure interference' that results from the combination or overlay of the axial and radial force components at the waist portion of the inflatable member in a pressurized state. In turn, stress inflection points are controllably formed, that induce a 'segmental inflection' of the lesion, enabling pressure to be directionally projected into the lesion and away from the vessel wall, and thereby, facilitating an atraumatic and controlled lesion cracking.

Figure 13:
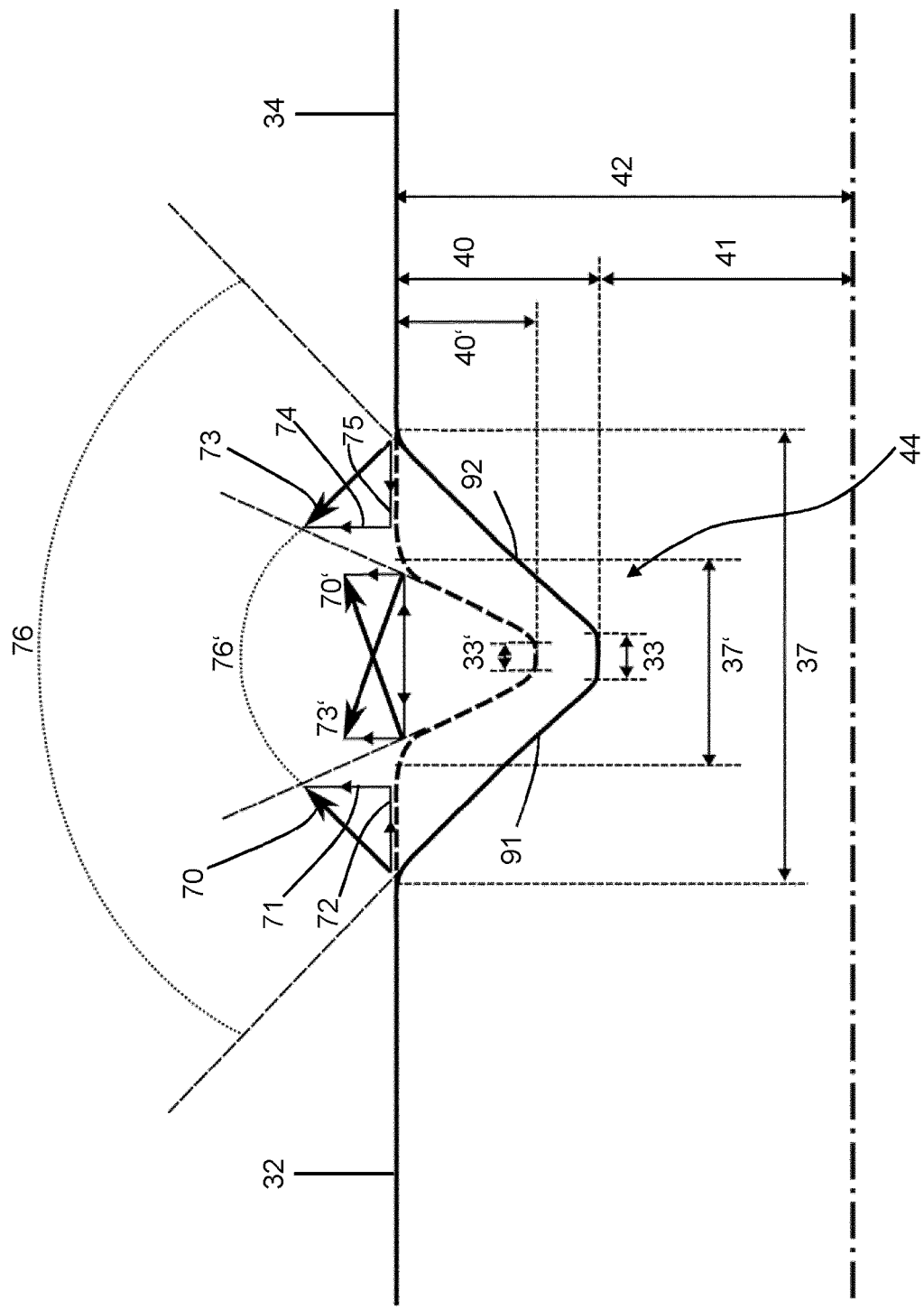
FIG. 13 illustrates a cross-lateral view of dimensional relationships of an inflatable member of the present disclosure characterizing a controlled direction of forces at different pressurization regimes in accordance with the present disclosure.

FIG. 13 illustrates a cross-lateral view of dimensional relationships of an inflatable member of the present disclosure characterizing a controlled direction of forces at different pressurization regimes, in accordance with the present disclosure. In FIG. 13, the outline of an inflatable member comprising at least two lobes 32, 34, and one or more waist portions 44 is depicted at a lower pressurization regime that is indicated as a black, continuous line, and at a higher pressurization regime that is depicted as a dashed line. The rotational axis of the inflatable member in turn is indicated as a dash-dotted line. Application of pressure, from an unpressurized or lower pressurization state to a pressurized or higher pressurization state, shifts the upper base of the waist portion 44 from a distance or depth 40 relative to the lower base of the waist portion 44 to a depth 40', and shifts the lower base from a distance or depth 41 above the rotational axis of the inflatable member to a depth 41'. Further, the lengths of the upper base 37 and the lower base 33 are compressed to the lengths 37' and 33'; and an angle 76 that is formed between the legs 91, 92 of the upper and lower base is changed to angle 76' upon pressurization. Application of pressure, from an unpressurized or lower pressurization state to a pressurized or higher pressurization state, changes the direction and magnitude of the directional force 70 (resulting from the vectorial addition of radial force component 71, and axial force component 72) and directional force 73 (resulting from the vectorial addition of radial force component 74, and axial force component 75) so that new directional forces 70' and 73' result. As becomes apparent from the change of magnitude and direction of the variable directional forces 70, and 73, upon pressurization, radial stress around the waist portion is directed away from the vessel wall and focalized into the lesion at an angle about perpendicular to the legs 91, 92 of the upper and lower base of the waist portion 44. As a specific effect of the variable directional forces conveyed between the lobes, waist portion and lesion, at different stages of pressurization, fracture planes are created along the direction of the directional forces that result in a controllable fracture of the lesion at multiple locations 67, 68 situated around the waist portion 44. At the same time concentrated radial stress is directed away from the vessel wall 65. The inventors now have found, that the above described effect of lesion fracture around the waist portion of the inflatable member can be maximized, when the waist portion 44 of the inflatable member has a length 37 (L) not greater than two times the radius 42 (R) of the inflatable member. In addition, the inventors have found, that decreasing or increasing, respectively changing the wall thickness 63 at the waist portion 44 in relation to the wall thickness 62 of the at least two or more lobes 32, 34 of the inflatable member changes a magnitude and direction of the variable directional forces 70, and 73 in a pressurized state. For example, decreased wall thickness 63 results in enhancing a magnitude of variable directional forces 70, 73 conveyed onto a portion 66 of the area to be treated 65 and further, results in a decrease of the angle 76 formed between the legs 91, 92, thereby increasing a corresponding incident angle that exists between the directional forces 70, 73. This surprisingly infers that the change of wall thickness 63 allows for controlling the angle at which the variable directional forces are focalized into the lesion, and thereby provides for an additional means to reliably control the depth, direction, location and number of lesion fractures. For further illustration, the specific technical effect of the segmentation of the inflatable member into the at least two or more lobes via one or more waist portions will be further described with reference to FIGS. 14-19.

Figures 14, 14A, 14B, 14C, 14D:
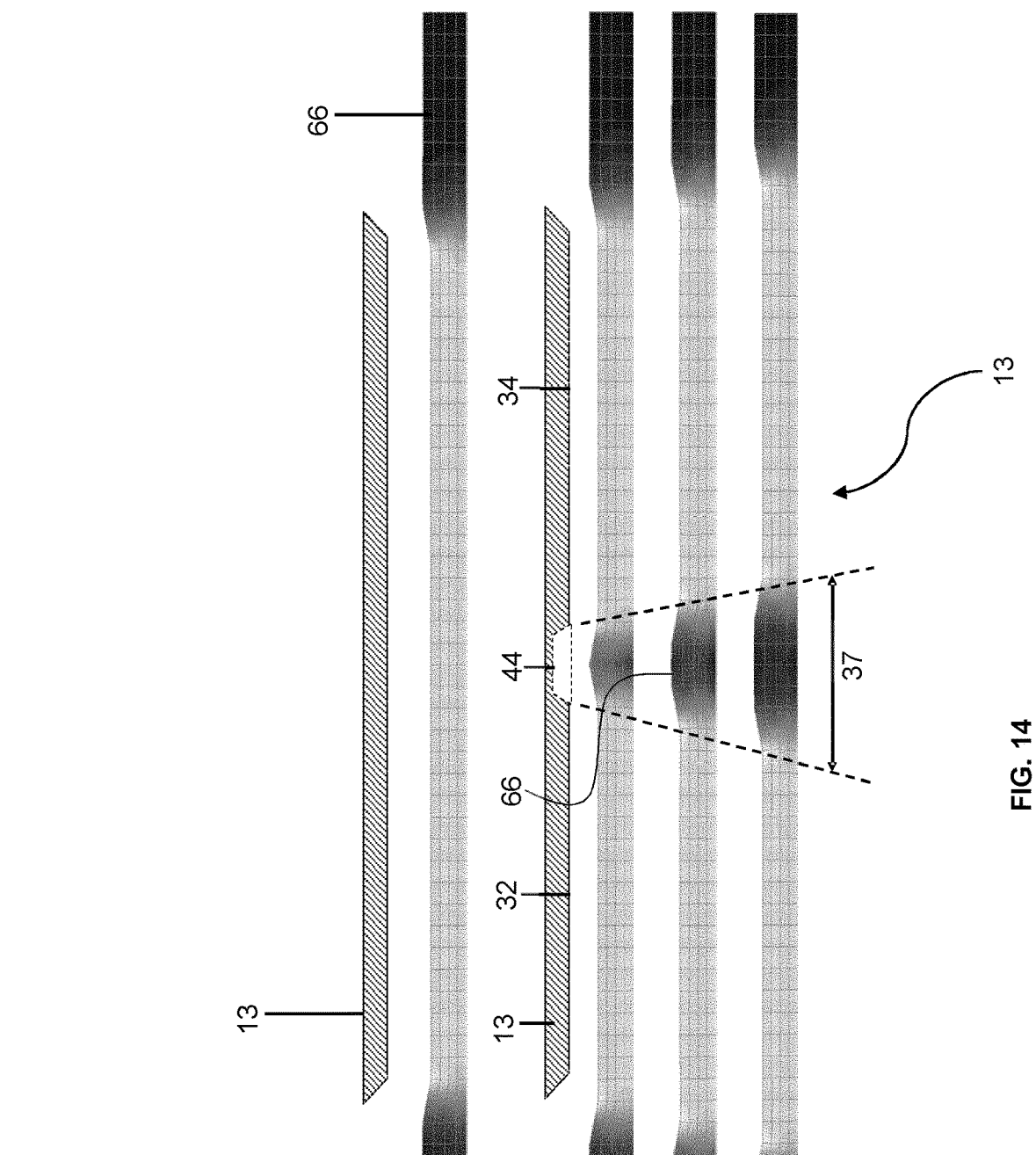
FIGS. 14A-14D are stress distribution diagrams resulting from forces applied to an obstructed vessel portion utilizing an inflatable member with variable waist portion lengths in accordance with the present disclosure.
Figures 15, 15A, 15B, 15C, 15D:
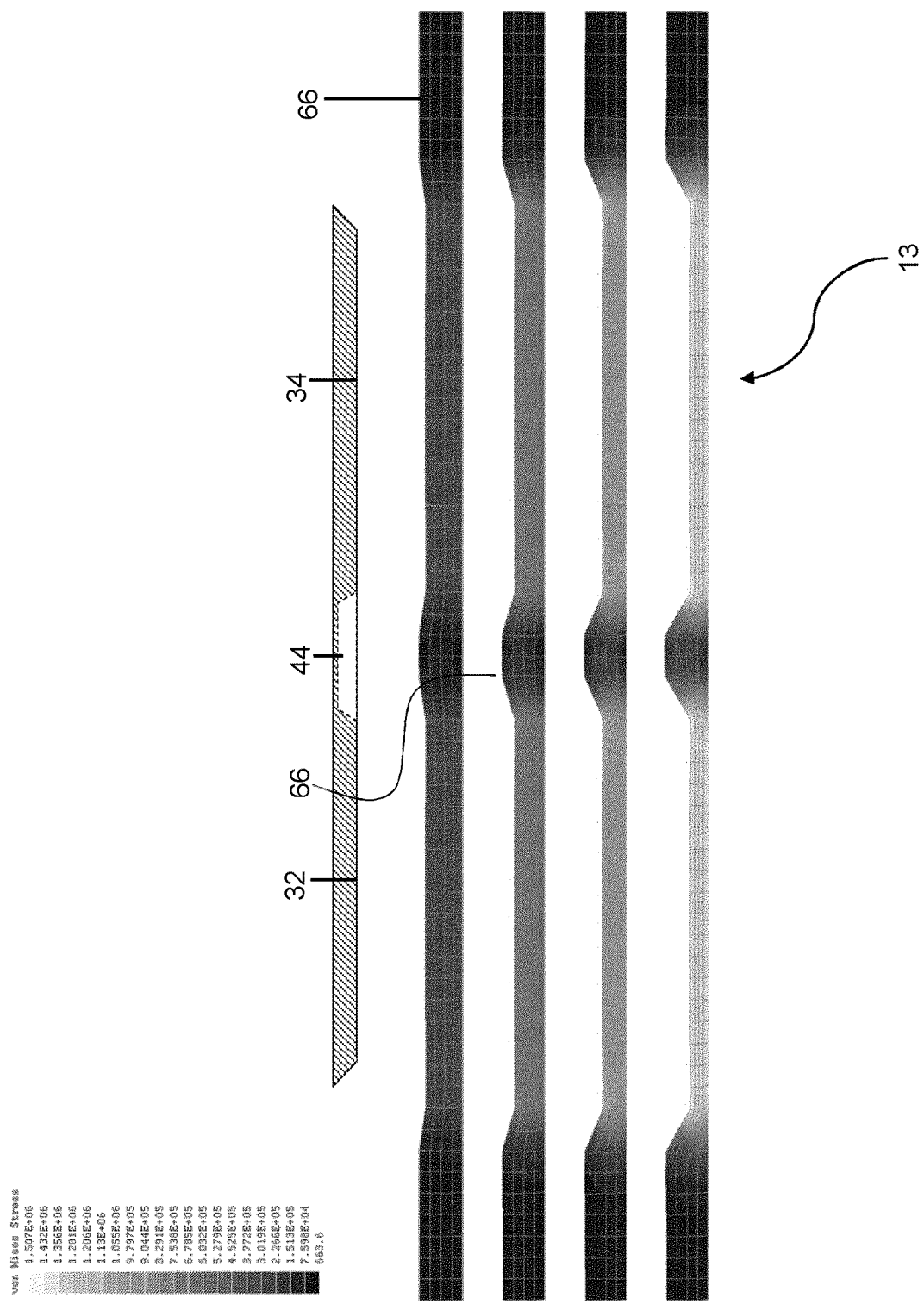
FIGS. 15A-15D are stress distribution diagrams resulting from different magnitudes of forces applied to an obstructed vessel portion utilizing an inflatable member in accordance with the present disclosure.

FIGS. 14A-14D are stress distribution diagrams resulting from forces applied to an obstructed vessel portion utilizing an inflatable member with variable waist portion lengths, in accordance with the present disclosure. FIG. 14A is a graphical representation of forces applied to a calcified lesion 66 by a single-membered, standard angioplasty balloon 13. The graphical representation shows the cross section of an angioplasty balloon 13, and the calcified lesion 66 with stress zones denoted in van Mises stress (MPa) over unit lengths (see legend). As shown in FIG. 14A, the conventional angioplasty balloon provides a generally uniform force to the lesion along its entire length. Because the stress is homogenously distributed, and because there is an absence of stress concentrator sites, conventional angioplasty catheters require the use of comparably high pressures to fracture a lesion. Further, these limitations contribute to a lack of uniform lesion fracture, such that the depth, direction, location and number of the lesion fracture(s) cannot be reliably controlled and/or an adequate patency of the vessel cannot be reliably achieved.

FIGS. 14B to 14D, are graphical representations of forces applied to a lesion utilizing an inflatable member design of FIGS. 2-8. Accordingly, in the provided examples, the inflatable member 13 includes at least two or more lobes 32, 34 and one or more waist portions 44. In FIGS. 14B, 14C and 14D, the waist portion length 37 of the inflatable member is varied from 2, 4 and 6 mm, as indicated by dashed lines, whereas the lengths of lobes 36, 38 each remain identical at 20 mm, and the diameter 43 of the inflatable member each remains identical at 6 mm. As can be observed from the stress distribution profiles generated around the waist portion, the change of stress intensity resulting from the overlay of directional forces, is dependent on the waist length, and is maximized when the waist portion 44 of the inflatable member has a length 37 (L) not greater than two times the radius 42 (R) of the inflatable member. Because the variable directional forces conveyed between the lobes and around the waist portion differ from the radial forces conveyed by the lobe portions of the inflatable member and a remainder of the area to be treated, radial stress is directed away from the vessel wall above the waist portion. The stress intensity around the waist portion is therefore lower than that of a conventional angioplasty balloon. Further, because a stress gradient is induced between the lobes and waist portion of the inflatable member, stress concentrator sites or inflection points are generated, that in turn result in the preferential formation of lesion fractures around the waist portion of the inflatable member, in analogy to the description provided in FIG. 13.

FIGS. 15A-15D are stress distribution diagrams resulting from different magnitudes of forces applied to an obstructed vessel portion utilizing an inflatable member in accordance with the present disclosure. In FIGS. 15A-15D, the inflatable member 13 includes at least two or more lobes 32, 34 and one or more waist portions 44. In the provided example, the waist length 37 is 4 mm, the lengths of lobes 36, 38 are 20 mm, and the diameter 43 of the inflatable member is 6 mm. In FIGS. 15A-15D, forces applied to the lesion 66 at different inflation pressures are varied from between 15 to 60 N, in 15 N increments each. As can be observed from the stress distribution profiles generated around the waist portion, the change of stress intensity resulting from the overlay of directional forces is dependent on the inflation pressure or force applied to the lesion. Because the variable directional forces conveyed between the lobes and around the waist portion differ from the radial forces conveyed by the lobe portions of the inflatable member and a remainder of the area to be treated, radial stress is directed away from the vessel wall. The radial stress intensity around the waist portion is therefore lower than that of a conventional angioplasty balloon. Further, because a stress gradient is induced between the lobes and waist portion of the inflatable member, stress concentrator sites or inflection points are generated, that in turn result in the preferential formation of lesion fractures around the waist portion of the inflatable member, in analogy to the description provided in FIGS. 13-14.

FIGS. 16A-16D are polariscope images illustrating the stress distribution in a lesion resulting from different amounts of pressurization of the inflatable member in accordance with the present disclosure. In each of the FIGS.

16A-16D, an inflatable member 13 includes at least two or more lobes 32, 34, and one or more waist portions 44. In the provided examples, the waist length 37 of the inflatable member is 3 mm each, and the diameter at nominal pressure (16 bar) is 3 mm each, whereas the lengths of lobes 36, 38 are each 80 mm. From left to right, in each of the FIGS. 16. A-16D, the inflatable member is in direct contact with a model lesion 66, and held in a pressurization state of 4, 6, 8 and 12 bar of pressure. A principal stress line 78 is observed in each of the images as a dark isochromatic line that incrementally bends away from the vessel wall and into the model lesion, at increasing inclinations, as the pressure is incrementally increased in 2 bar steps. The principal stress lines 78 are oriented in the same direction as the direction of the cleavage planes 67, 68, as exemplarily referenced in FIG. 12. In turn, stress concentrator sites, or stress inflection points are controllably generated at the waist portion 44, visible as an alternation of regions of dark and light contrast, that in turn favorably fracture the lesion 66, as desired. In the provided example, when the pressure is increased, the principal stress lines bend away from the vessel wall and into the lesion at angles that correspond to the angles 76, 76' of FIG. 12. Hence, as a specific technical effect of the segmentation of the inflatable member into the at least two or more lobes via one or more waist portions, variable directional forces are created, that when conveyed between the lobes, waist portion and lesion, at different stages of pressurization, create cleavage planes along the direction of the variable directional forces, that in turn result in a controllable fracture of the lesion at multiple locations situated around the waist portion.

FIGS. 17A-17D and FIGS. 18A-18D are polariscope images illustrating the stress distribution in a lesion resulting from different amounts of pressurization of inflatable members manufactured by balloon blowing, and balloon blowing and thermoforming, respectively, in accordance with the present disclosure. In FIGS. 17A-17D, the inflatable member has been manufactured by a single-stage balloon blowing process. In the example of FIG. 17A-17D, when the inflatable member is manufactured by a single-stage balloon blowing process, a second wall thickness (62) exemplarily ranges from about 0.020-0.025 mm, and a third wall thickness (63) exemplarily ranges from about 0.025-0.050 mm. Thereby, in reference to FIG. 11A, the first wall thickness (61) of the inflatable member exceeds the second wall thickness (62), and the third wall thickness (63) exceeds the second wall thickness (62). In comparison, in FIGS. 18A-18D, the inflatable member has been manufactured by a first-stage balloon blowing process and a second stage thermoforming process. Thereby, in reference to FIG. 11B, the first wall thickness (61) exceeds the second wall thickness (62), and the second wall thickness exceeds the third wall thickness (63).

In each of the FIGS. 17A-17D and FIGS. 18A-18D, an inflatable member 13 includes at least two or more lobes 32, 34, and one or more waist portions 44. In the provided examples, the waist (or lower base) length 37 of the inflatable member is 1 mm each, and the diameter at nominal pressure (16 bar) is 3 mm each, whereas the lengths of lobes 36, 38 are each 20 mm. From left to right, in each of the FIGS. 17A-17D and FIGS. 18A-18D, the inflatable member is in direct contact with a model lesion 66, and held in a pressurization state of 4 bar (A), 6 bar (B), 8 bar (C) and 12 bar (D) of pressure. A principal stress line 78 is observed in each of the images as a dark isochromatic line or fringe that incrementally bends away from the vessel wall and into the model lesion, at increasing inclinations, as the pressure is incrementally increased in 2 bar steps. As can be observed from the direct comparison of FIG. 17A-17D with FIG. 18A-18D, in the case of inflatable members manufactured by a first-stage balloon blowing process and a second stage thermoforming process, additional principal stress lines or fringes are present at equal amounts of pressurization (FIG. 18D). This indicates, that at equal amounts of pressurization, the stress distribution profiles for the inflatable members produced by the two different manufacturing processes are different, and further, that a stress loading state when the first wall thickness (61) exceeds the second wall thickness (62), and the second wall thickness (62) exceeds the third wall thickness (63) is higher than a stress loading state, when the first wall thickness (61) exceeds the second wall thickness (62), and the third wall thickness (63) exceeds the second wall thickness. Thereby, a magnitude of variable directional forces 70, 73 conveyed onto a portion 66 of the area to be treated 65 is enhanced. As a result, a change of the wall thickness 63 of the one or more waist portions 44, 45 changes a magnitude and direction of the variable directional forces 70, and 73, such that the depth, direction, location and number of lesion fractures is reliably controlled.

In alternate implementations, and in reference to FIGS. 11A-B, it is further contemplated, that one or more third wall thickness 63 of the one or more waist portions 44, 45 of the at least two lobes 32, 34 of the inflatable member 10 can be varied with respect to the first (61) and second wall thickness (62), such that when combined, can result in a favorable combination of improved axial stability and increase of the magnitude of variable directional forces created at the waist portions. For example, a balloon catheter 10 comprising an inflatable member 13 having a distal predilatation portion and a proximal dilatation portion can consist of a predilatation portion that is manufactured by a two-stage balloon blowing and thermoforming process, and a proximal dilatation portion manufactured by a single stage balloon blowing process. Thereby, the distal predilatation portion can exhibit a favorable increase of the magnitude of variable directional forces at the waist portions across the length of the distal predilatation portion, and the proximal dilatation portion can exhibit an improved axial stability across the length of the proximal dilatation portion.

FIGS. 19A-19D are polariscope images illustrating the stress distribution in a lesion resulting from a variation of the waist portion length at equal amounts of pressurization of the inflatable member in accordance with the present disclosure. In FIGS. 19A-19D, an inflatable member 13 includes at least two or more lobes 32, 34, and one or more waist portions 44. In the provided examples, the waist portion length 37 of the inflatable member is varied, from left to right, from 1 mm (A), 2 mm (B), 4 mm (C) and 6 mm (D). The diameter at nominal pressure (16 bar) is 3 mm each, whereas the lengths 36, 38 of the lobes 32, 34 are 20 mm each. In each of the FIGS. 19A-19D, the inflatable member is in direct contact with a model lesion 66, and held in a pressurization state of 8 bar of pressure. In FIGS. 19A and 19B, an overlapping or mutual principal stress line 78, visible as a dark isochromatic line or fringe that incrementally bends away from the vessel wall and into the model lesion is formed between the adjacent lobes 32, 34 of the inflatable member. In FIGS. 19C and 19D, such principal stress 78 line is absent. As a result, when the waist portion length L (37) does not exceed two times the radius R (42) of the inflatable member in a pressurized state, principal stress lines can optimally overlap or form between the at least two or more adjacent lobes 32, 34 of the inflatable member, whereas, when the waist portion length exceeds two times the radius R (42) of the inflatable member, such concerted interaction is absent, or only present at higher, and thus less desired states of pressurization. Hence, when one or more of the waist portion 44, 45 of the at least two lobes 32, 34 of the inflatable member 13 comprises a length L (37) not greater than two times the radius R (42) in a pressurized state, stress inflection points are controllably induced, that [result in a pressure interference and segmential inflection and] result in the preferential formation of lesion fractures 67, 68 at each waist portion 44 of the inflatable member, thereby maximizing the effect of lesion fracture around the waist portion of the inflatable member.

Figure 20A:
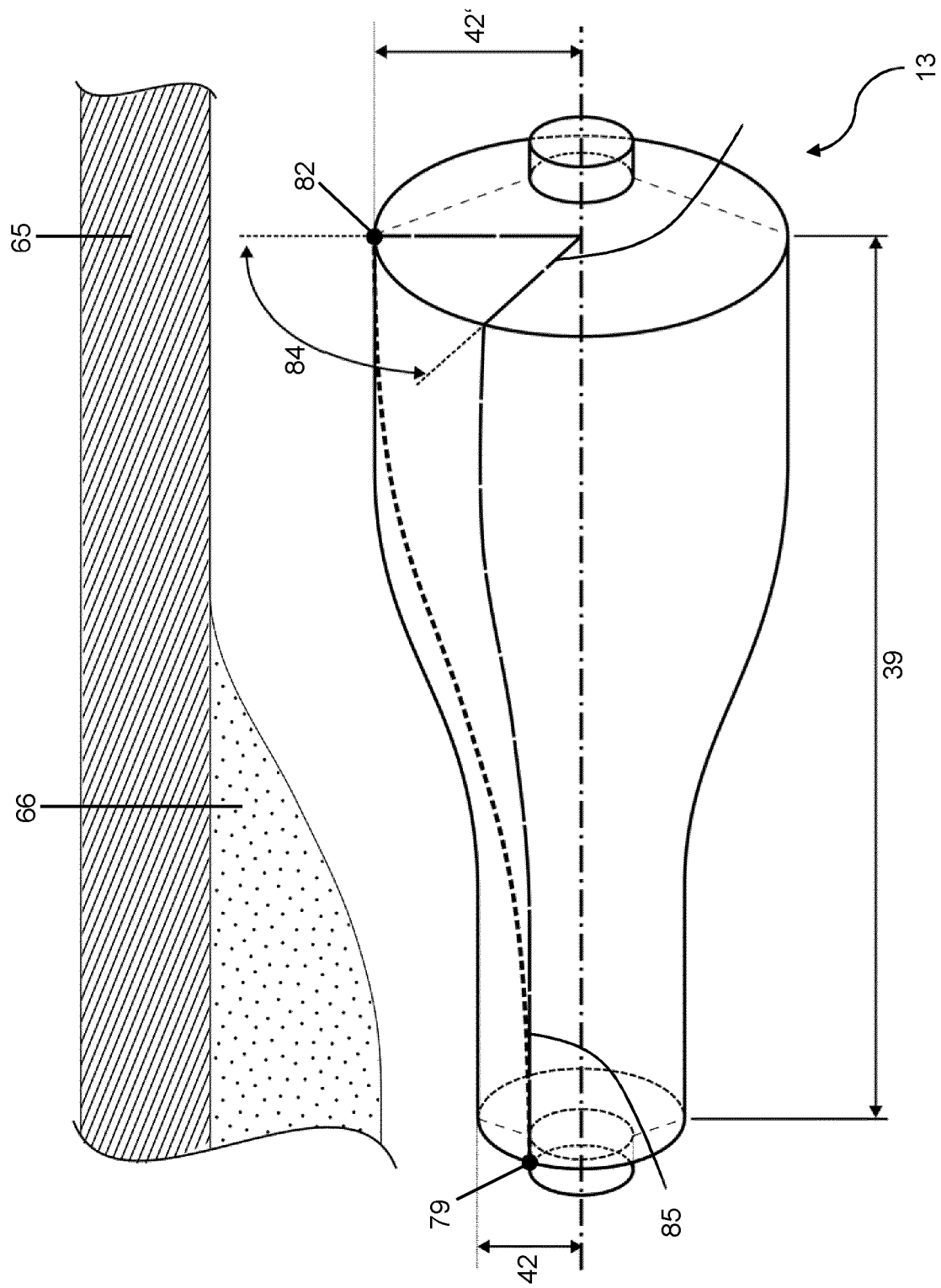
FIGS. 20A-20B are graphical representations of torsional loads applied to a treatment area by a conventional inflatable member (A) versus an inflatable member comprising at least two or more lobes (B) in accordance with the present disclosure.
Figure 20B:
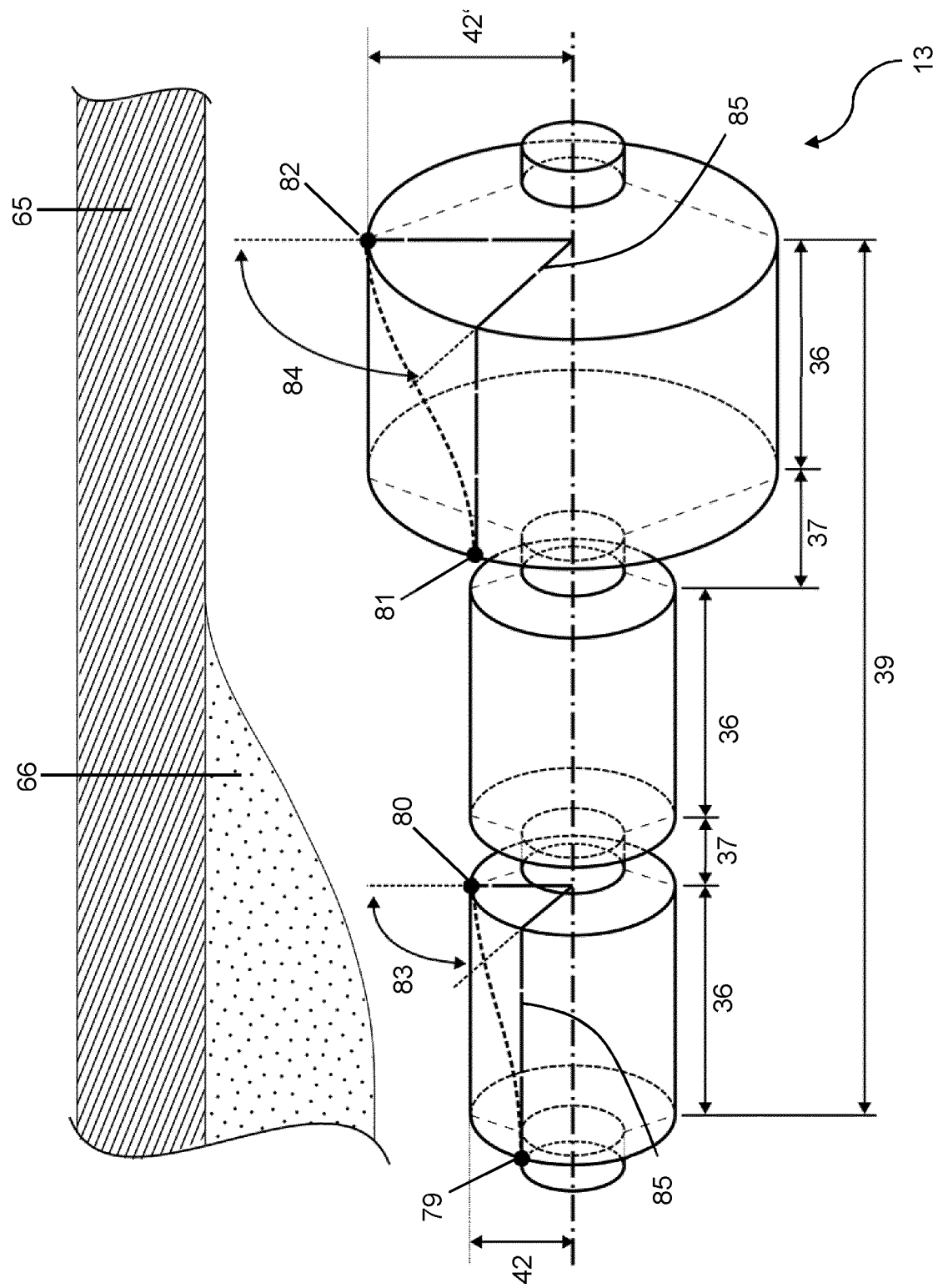

It has been further found by the inventors that an inflatable member comprising at least two or more lobes and one or more waist portions in accordance with the present disclosure is able to distribute and thereby reduce an amount of torsional load that is generated during unfolding of the at least two or more lobes that can be transmitted between the inflatable member, lesion and surrounding area of treatment, as compared to a conventional single-membered balloon. For further illustration, FIGS. 20A-20B provide graphical representations of torsional loads applied to a treatment area by a conventional inflatable member (A) versus an inflatable member comprising at least two or more lobes (B) in accordance with the present disclosure. In FIGS. 20A-20B, a partially folded and pleated inflatable member 13 is shown in contact to a lesion 66 located in a blood vessel 65. FIG. 17A comprises a conventional, single inflatable member, whereas FIG. 17B depicts an inflatable member comprising a distal, middle and proximal lobe and two waist portions according to the current disclosure. In each case, the distal end of the balloon is shown dimensionally constrained and held at a radius 42 in a partially inflated state, and the proximal end is held unconstrained by the blood vessel and in an inflated state having a radius 42'. Further, pleat lines 85, indicated as a long-dash line, are shown on the distal and proximal lobes, with each having a starting position 79, 81 in an uninflated state, that when inflated, rotate by an unfolding angle 83, and 84, respectively.

However, when the two different types of inflatable members are inflated, in FIG. 20A, inflation of the conventional, single membered angioplasty balloon creates a torsional load between the fix points 79 and 82, across the entire length of the balloon, whereas in FIG. 20B the distal lobe generates a torsional load between the fix points 79, and 83, and the proximal lobe creates a torsional load between the fix points 81, 82. As a result, in FIG. 20B, because the length of individual lobes 36 of the inflatable member 13 of the present disclosure is reduced, the torque of the individual lobes is also reduced to the same extent. The total sum of the individual torques of the individual lobes cannot exceed the torque that would be otherwise generated over an entire length of a balloon. Therefore, the inflatable member comprising at least two or more lobes and one or more waist portions in accordance with the present disclosure is able to reduce an amount of torsional load that is generated during unfolding of the at least two or more lobes that can be transmitted between the inflatable member, lesion and surrounding area of treatment. In addition, the torsional load generated by each lobe is interrupted at each waist portion. As a result, the generation of torsional loads of an inflatable member of the current disclosure remains localized at the individual lobes, reducing potential damage that could occur from torsional loading over an entire length of a lesion, as would be the case if a single-membered balloon construction of the same length and diameter were to be used.

Based on the foregoing description, the balloon catheter 10 according to the current disclosure, comprising:
  an elongated member 15 having a proximal end 19, a distal end 12 and at least one lumen 25, 26 extending at least partially through the elongated member; and
  an inflatable member 13 affixed to the elongated member adjacent to the distal end and in fluid communication with the at least one lumen 26, the inflatable member having a radius R (42) and including at least two lobes 32, 34, the at least two lobes separated from each other by one or more waist portion 44, 45;
  wherein in an unpressurized state, the at least two lobes 32, 34 of the inflatable member 13 are provided each folded and pleated, such that subsequent pressurization of the inflatable member individually unfolds each of the two or more lobes;
  demonstrates that, in a pressurized state, a segmentation of the inflatable member into the at least two or more lobes:
  distributes, and thereby reduces a torsional load 79, 82 that is transferred between the inflatable member and an area to be treated 65, 66;
  controllably conveys opposing axial forces 72, 75 between the lobes (at the waist portion), and thereby reduces an amount of axial load that is transferred between the inflatable member and an area to be treated; and
  controllably conveys equidirectional radial 71, 74 forces between the lobes 32, 34 and around the waist portion 44 that differ in magnitude from the radial forces conveyed by the lobes, and thereby directs away radial stress from a vessel wall 65 around the waist portion 44;
  characterized in that the combination of the opposing axial 72, 75 and equidirectional radial 71, 74 forces around the waist portion 44 create variable directional forces 70, 73 that, when conveyed onto a portion 66 of the area to be treated 65, controllably induce stress inflection points that [result in a pressure interference and segmential inflection and] result in the preferential formation of lesion fractures 67, 68 at each waist portion 44 of the inflatable member.

In the above, the one or more waist portion 44, 45 of the inflatable member 13 comprises one or more length L (37) selected from at least a set of ranges that includes 0-20 mm, 1-2 mm, 2-4 mm, 4-6 mm, 6-8 mm, 8-10 mm, 10-12 mm, 12-14 mm, 14-16 mm, 16-18 mm, and 18-20 mm. Preferably, the one or more waist portion 44, 45 of the inflatable member 13 comprises a length L (37) not greater than two times the radius R (42) in a pressurized state, so as to controllably induce stress inflection points that [result in a pressure interference and segmential inflection and] result in the preferential formation of lesion fractures 67, 68 at each waist portion 44 of the inflatable member.

Further, in a pressurized and lesion-contacting state, the waist portion between the at least two lobes of the inflatable member and an area to be treated 65, 66 forms an impact zone that is substantially shaped as a trapezoid;
  wherein the trapezoid shape includes:
    an upper base having a first length 37 that is equivalent to the length of the waist portion;
    a lower base having a second length 33 smaller than the first length;
    a first depth equivalent to a radial distance 40 between the upper base and the lower base;

a second depth equivalent to a radial distance 41 between the lower base and a rotation axis of the inflatable member;

two legs 91, 92 formed at an angle 76 that is defined by the (first and second) lengths 37,33 and radial distances 40,41 between the lower and upper base, wherein a sum of the first and second depths 40, 41 are equivalent to an outer radius 42 of the inflatable member, and wherein the first depth is equivalent to the depth of the waist portion.

Further, in the above, a change of the third wall thickness 63 of the one or more waist portions 44, 45 changes a magnitude and direction of the variable directional forces 70, and 73, such that the depth, direction, location and number of lesion fractures is reliably controlled.

With respect to the preceding, a third wall thickness 63 at the waist portion 44, 45 of the at least two lobes 32, 34 of the inflatable member 13 of the balloon catheter 10 of the present disclosure can be varied with respect to the first and second wall thickness, such that at least one of the axial stability and a magnitude and direction of the variable directional forces 70, and 73 is reliably controlled. In other words, the one or more third wall thickness 63 of the waist portion 44, 45 of the at least two lobes 32, 34 of the inflatable member 13 of the balloon catheter 10 of the present disclosure can consist of multiple, different wall thicknesses 63, wherein the first wall thickness 61 of the inflatable member exceeds the second wall thickness 62, and the second wall thickness exceeds the third wall thickness 63, or wherein the first wall thickness 61 of the inflatable member exceeds the second wall thickness 62, and the third wall thickness 63 exceeds the second wall thickness.

Static and Pulsatile Modes of Angioplasty Catheter Operation

Conventional modes of operation of current balloon catheters include inflation of the balloon using standard inflation devices. The balloons are manually inflated to a pressure regime between a nominal pressure and below rated burst pressure, held for short dwell time at a static (or constant) pressure, and subsequently, deflated and withdrawn from the patient. Given the limitations of current angioplasty balloon catheter systems and available angioplasty treatment procedures, it is therefore further contemplated, that the angioplasty catheter of the current disclosure is preferably operated with a pulsatile, and/or modulated pressure regime. The pulsatile pressure modulation is intended to enhance and/or facilitate fracture formation within the area of treatment by superimposing a dynamic pressure modulation onto the inflatable member during use. Pulsatile pressure modulation can afford additional benefits through additional generation of vibrational modes acting on the inflatable member and lesion. Depending on the shape of the inflatable member, and the underlying lesion geometry, specific modes can be generated in both inflatable member and lesion, thereby allowing the controlled formation of variable directional forces at the waist portion of the inflatable member and permitting the delivery of focalized pressure to complex lesions without having the limitations or drawbacks of the known angioplasty catheter systems and procedures. The static and pulsatile modes of operation will be next described with reference to FIGS. 21-22.

Figure 21:
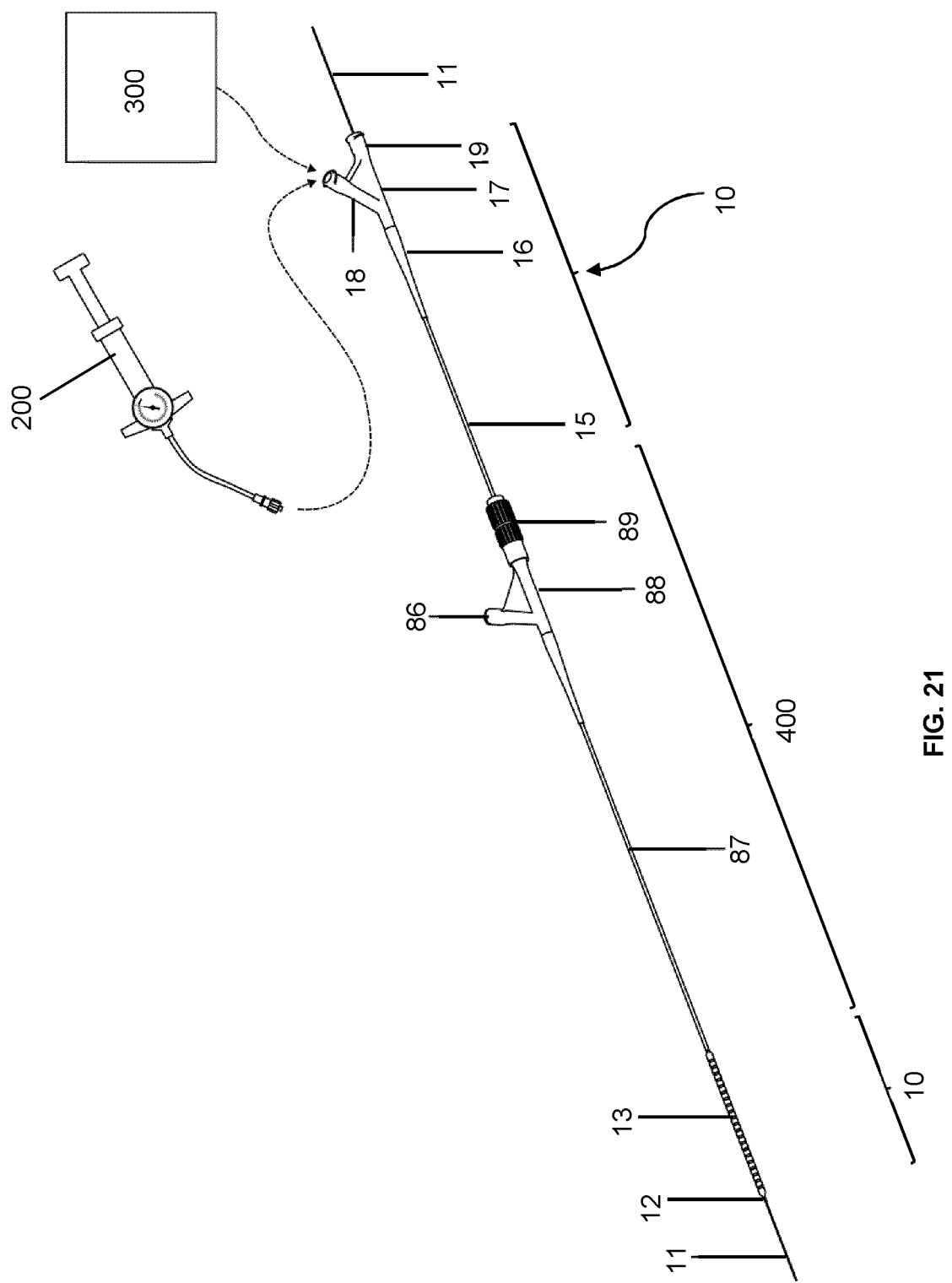
FIG. 21 illustrates a perspective view of an angioplasty balloon catheter of the present disclosure and adjunct devices for performing an angioplasty treatment in accordance with the present disclosure.

For further illustration, FIG. 21 provides a perspective view of an angioplasty balloon catheter and adjunct devices for performing an angioplasty treatment in accordance with the present disclosure. In FIG. 21, an angioplasty catheter system 10 is shown inserted into a support catheter 400 that in turn comprises a manifold 88, a hemostatic valve 89, a flushing port 86, and a support catheter shaft 87. The support catheter 400 can be used in conjunction with the balloon catheter 10 of the current disclosure to provide for additional substantial structural guidance and support as an external tubular shield that reduces potential vessel damage during transport and maneuvering operations. Further, the support catheter can provide length-adjustability to an inflatable member 13 of the balloon catheter 10, if so desired. The inflatable member 13 of the angioplasty catheter extends beyond the distal edge of the support catheter shaft, and is routed over a guide wire 11, that in turn extends from the tip of the angioplasty catheter balloon 12 to a guide wire port 19. The inflation port 18 can be operationally coupled to a standard inflation device 200, and operated by manual control, or preferably operationally coupled to a pressure generator 300 that is capable of generating a programmable, pulsatile pressure modulation, as described previously. Accordingly, the pressure generator 300 suitable for pulsatile pressure modulation may modulate one or more of a phase, an amplitude, a frequency, a pulse, a period, a pressure, and a shape of a pressure profile, when operationally coupled to the inflatable member. Because the pressure generator 300 is operatively coupled to the inflatable member 13 of the balloon catheter 10 via the inflation port 18, the pressure generator 300 is directly in fluid communication with the inflatable member 13 via the inflation lumen located inside the catheter shaft 15. In a preferred implementation, the pressure generator 300 is a singular device capable of modulating a pressure regime inside the inflatable member 13. Alternatively, in one implementation, the balloon catheter 10 is operatively connected to an inflation device 200 and the inflation device is coupled to an additional pressure generator 300, that in turn overlays a modulated pulsatile pressure profile onto e.g. a static pressure regime generated by the inflation device. In other possible implementations, the pressure generator 300 is directly integrated into the inflation device. Yet still, the pressure generator can be directly integrated into the inflatable member 13, for example in the form of an electrohydraulic or ultrasound emitter. The pressure generator 300 is preferably selected from a group consisting of: an inflation device, a mechanic pressure transducer, a hydraulic pressure transducer, an electro-hydraulic pressure transducer, an ultrasound transmitter, a lithotripsy emitter, a pump and/or suitable combinations formed therefrom. Pressure generators and/or pumps can include without limitation, rotary pumps, piston pumps, gear pumps, peristaltic pumps, piezo-driven pumps, or in general, any device capable of pulsatile pressure modulation in accordance to the present disclosure.

Summarizing the above, the balloon catheter 10 according to the disclosure can include a pressure generator 300 suitable for pulsatile pressure modulation that modulates one or more of a phase, an amplitude, a frequency, a pulse, a period, a pressure, and a shape of a pressure profile when operationally coupled to the inflatable member. In the above, the pressure generator 300 is selected from a group consisting of: an inflation device, a mechanic pressure transducer, a hydraulic pressure transducer, an electro-hydraulic pressure transducer, an ultrasound transmitter, a lithotripsy emitter, a pump and combinations formed therefrom. Further, the pressure generator 300 can be provided integrated into the inflation device. Such balloon catheter 10, as described in the underlying disclosure, is intended for further medical use in complex lesion treatment and for intramural drug delivery.

Controlled Percutaneous Angioplasty Procedure (C-PTA)

Different types of vascular interventional procedures and devices have been developed over the past decades to render treatment for various manifestations of arteriosclerotic disease. First generation balloon angioplasty procedures ('plain old balloon angioplasty', or "POBA"), typically carried out at pressures in the range of 6-8 bar over a period of a few minutes transiently achieve reperfusion of narrowed vessels by increasing luminal vessel diameter predominantly through plaque compression. Second generation angioplasty procedures, typically carried out at higher pressure ranges on the order of about 12-16 bar and over much shortened time periods of usually less than a minute, facilitate reperfusion of narrowed vessels and complex lesions predominantly by breaking up the lesion, followed by compression and/or displacement of the fractured lesion. While both first and second generation balloon angioplasty can suffer from acute elastic recoil, abrupt vessel closures and dissection, elastic recoil is less pronounced in second generation angioplasty procedures, whereas dissections tend to be more pronounced as a result of applying higher pressures. However, balloon angioplasty remains limited due to abrupt vessel closure that necessitates emergency bypass surgery in about 2 to 3% of patients, and restenosis that requires repeat revascularization in 30 to 50% of patients. Newer, next generation balloons including cutting balloons and scoring balloons have so far not been entirely successful in improving procedural efficacy in treating complex lesions, and, given an inherently higher potential for causing vessel trauma, are not likely to exceed post-procedural vessel patency rates of conventional balloon angioplasty catheters. The inventors of the present disclosure have contemplated a novel procedural approach for performing an angioplasty procedure that utilizes a combination of angioplasty balloon catheters of the present disclosure, and adjunct devices capable of performing pulsatile pressure modulation. The combination results in a controlled percutaneous transluminal angioplasty procedure (short: C-PTA), wherein optimized pulsatile pressure profiles are applied over various phases of the treatment procedure in conjunction with the angioplasty catheters of the current disclosure.

Figure 22:
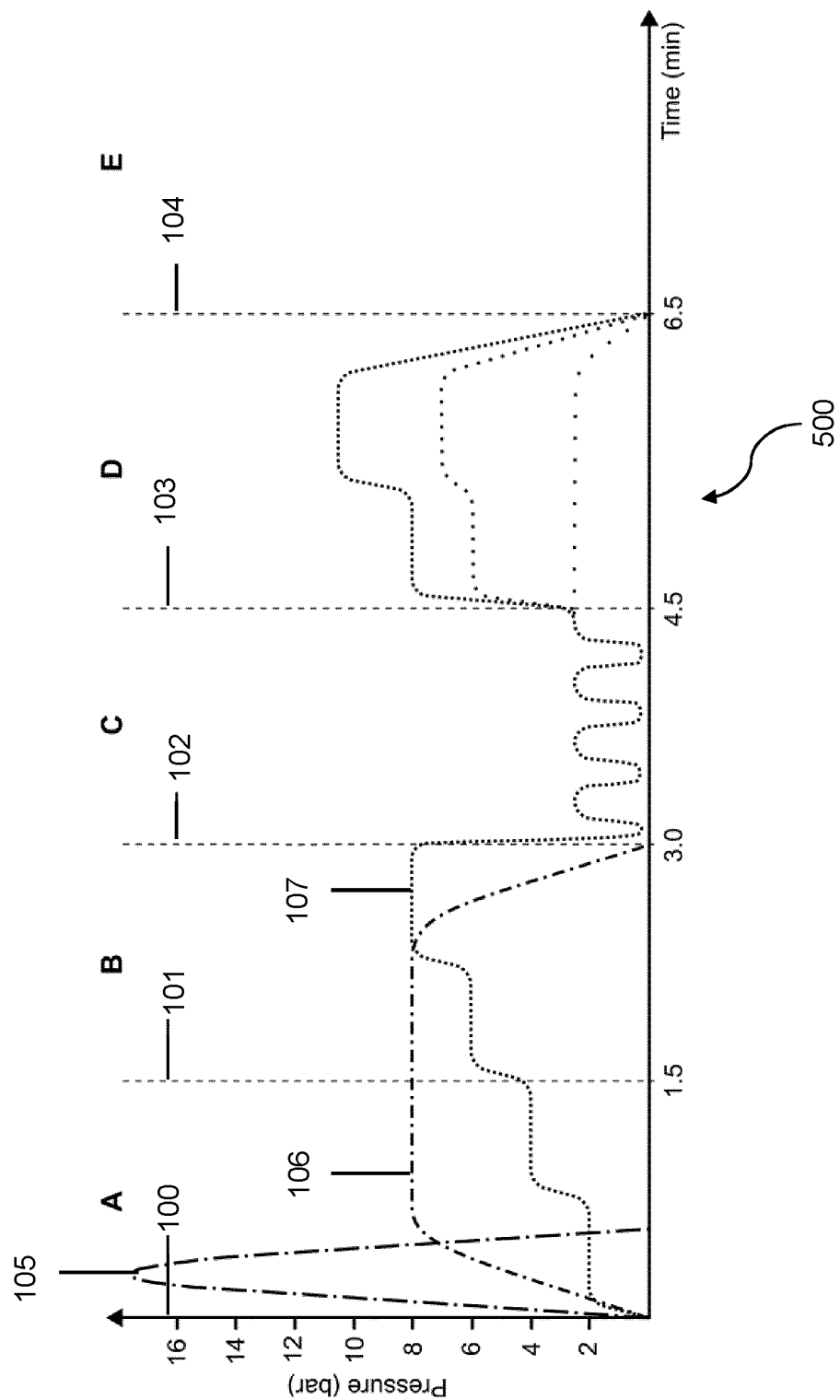
FIG. 22 illustrates a series various phases of performing an angioplasty treatment in accordance with the present disclosure.

For further illustration, FIG. 22 provides a series of various phases of performing an angioplasty treatment in accordance with the present disclosure. In FIG. 22, a diagram 500 denotes various pressure profiles that can be applied over the course of time of an angioplasty procedure. The Y-axis of the diagram is provided as pressure in bar units, and the X-axis is provided as procedural time in minutes. A first exemplary pressure profile 106, indicated as a short dash-dotted line, depicts a pressure profile of a first generation POBA angioplasty procedure, wherein an angioplasty balloon is inflated to a pressure of about 8 bar over the course of about 0.5 to 1 minutes, and held within a lesion to be treated for about up to 3 minutes, followed by deflation and removal from the patient. A second exemplary pressure profile 105, indicated as a long dash-dotted line, shows the typical progression of a second generation high pressure angioplasty procedure, wherein an angioplasty balloon is inflated to a pressure of about or exceeding 16 bar, and held within an area of treatment over a relatively short period of about 0.5 to 1 minutes, followed by deflation and removal from the patient. The angioplasty procedure according to the present disclosure separates the treatment procedure into multiple phases, and provides specific pressure profiles or regimes that are tailored to each phase. The phases are indicated on the diagram as letters A-E and demarcated on the X-Axis by dashed lines. The multi-stage angioplasty procedure comprises a series of phases, including a conditioning phase (A), a controlled lesion cracking phase (B), a mobilization phase (C), a lesion modelling phase (D) and an optional or supplemental drug delivery phase (E).

The modulated pressure profiles that are applicable in each phase of the improved angioplasty procedure, are indicated by a dotted line 107, and exemplarily performed as follows:

Phase (A): The first, or conditioning phase 100, consists of incrementally ramping up the pressure of the inflatable member, exemplarily in 1-3 bar increments, preferably about 2 bar increments, over an exemplarily period of between 1-2 minutes, preferably about 1.5 minutes, to a first pressure plateau, exemplarily between 2-4 bar, preferably about 4 bar. Phase A is intended to slowly unfold and atraumatically inflate the balloon to the dimensions of a target area to be treated, apposing the balloon to the lesion, 'stretching' the smooth muscle cells of the vessel wall, and mechanically fatiguing the lesion/plaque, thereby conditioning the lesion and initializing dilation of the lesion. The inflatable member is slowly stabilized or seated in the lesion, and inflated to a low pressure regime (about 2-4 bar) that is atraumatic with respect to potential formation of ruptures, dissections or distensions that are typically observed in high pressure angioplasty procedures. The time period for performing conditioning is selected such that the smooth muscle cells can adequately adapt to the tension exerted by the balloon, and the plaque mechanically is fatigued at the low pressure regime (about 1-2 min).

Phase (B): The second, or controlled lesion cracking phase 101, consists of incrementally ramping up the pressure of the inflatable member, exemplarily in 1-3 bar increments, preferably about 2 bar increments, over an exemplarily period of between 1-2 minutes, preferably about 1.5 minutes, from the first pressure plateau, exemplarily of 2-4 bar, preferably about 4 bar to a second pressure plateau, exemplarily of 6-10 bar, preferably about 8 bar. Phase B is intended for performing controlled lesion cracking, using the inflatable member of the current disclosure, wherein the application of focalized pressure to a lesion results in a controllable fracture of the lesion at preferably multiple locations. Segmentation of the inflatable member into the at least two or more lobes induces a 'pressure interference' that results from the combination or overlay of the axial and radial force components at the waist portion of the inflatable member in a pressurized state. In turn, stress inflection points are controllably formed, that induce a 'segmental inflection' of the lesion, enabling pressure to be directionally projected into the lesion and away from the vessel wall, and thereby, facilitating an atraumatic and controlled, sequential lesion cracking. The applicable pressure regime (about 6-10 bar) is lower by design of the inflatable member of the current disclosure and consistent with the atraumatic pressure regimes of first generation POBA angioplasty catheters, which in turn are lower than second generation and high pressure balloon angioplasty catheters, and yet, suitable for compressing and displacing fibrous plaque, as well as for controllably cracking calcified plaques in complex lesions. As a result of the applied lower pressure regimes, risk of more severe dissections are reduced. The time period for performing controlled lesion cracking is selected such that the lesion/plaque continues to remain adequately mechanically fatigued at the low pressure regime (about 1-2 min).

Phase (C): The third, or mobilization phase 102, consists of ramping down the pressure from the second pressure plateau, exemplarily of 6-10 bar, preferably about 8 bar, to a substantially depressurized state of the inflatable member, but without losing intimal contact to a lesion, exemplarily 0-2 bar, preferably about 0 bar, and alternatingly modulating the pressure between about 0 bar and a third pressure plateau, exemplarily of 1-3 bar, preferably about 2 bar, over an exemplary period of about 1-3 minutes, preferably 1.5 minutes. Phase C is intended to mobilize the blood flow to the treatment area and/or diseased vessel portion and to relieve built-up stress in the vessel, by temporarily relaxing and tensioning the vessel diameter. The oscillating motion of the balloon serves to 'warm up' respectively 'activate' the substantially dormant smooth muscle cells in the vessel wall at a low pressure regime, thereby facilitating increased oxygenation of the cells, and promoting subsequent revascularization of the vessel. The mobilization phase in turn prepares the vessel for the subsequent lesion modelling phase D.

Phase (D): The fourth, or lesion modelling phase 103, consists of ramping up the pressure from the third pressure plateau, exemplarily of 1-3 bar, preferably about 2 bar, to a fourth pressure plateau, exemplarily 6-10 bar, preferably about 8 bar, and holding the pressure plateau, exemplarily for a period of 0.5-2 minutes, preferably 1 to 1.5 minutes, followed by ramping up the pressure to a fifth pressure plateau, exemplarily 8-14 bar, preferably about 10 to 12 bar, and holding the pressure plateau for a period, exemplarily of 0.5-2 minutes, preferably 1 to 1.5 minutes, followed by slow deflation to an end pressure of 0 bar over a period, exemplarily of 0.25 to 1 minutes, preferably of about 0.5 minutes. Phase D is intended to finalize the three-dimensional re-modelling of the vessel at a nominal diameter of the inflatable member. The inflatable member that has been seated in the lesion is inflated to its nominal diameter at a nominal pressure, using the compliance characteristics of the balloon to finalize the vessel geometry. The time period for performing modelling is selected such, that the vessel wall including smooth muscle cells can adequately adapt to the nominal diameter of the inflatable member (about greater than 1-2 min), thereby stabilizing the vessel wall including the smooth muscle cells, as well as the vessel diameter and thereby, reducing vessel recoil post modelling phase.

Phase (E): The drug delivery phase 104 is an optional or supplemental phase carried out prior to, during, or after the series of phases A-D have been completed, using for example an inflatable member as described in FIG. 7 of the present disclosure. Phase E is intended to further improve the clinical long-term effectiveness of the angioplasty procedure through the administration of therapeutic agents, that can help accelerate healing, prevent inflammation, suppress restenosis of the diseased vessel portion, among other possible indications.

The above described multi-phase angioplasty procedure favorably combines the advantages of the first and second generation angioplasty procedures without having their specific drawbacks, and thereby, enables a high-quality, controlled percutaneous transluminal angioplasty (C-PTA).

The specific pressure regimes, as well as the specific time periods for ramping up, maintaining pressure and ramping down in the aforementioned angioplasty procedure are of exemplary nature and not intended to be limiting. The specific pressure regimes and time periods may vary according to additional procedural factors and clinical indication, including vessel anatomy, length and diameter of device and lesion, among others.

Summarizing the described method for treating a vascular pathology with a balloon catheter 10 according to the underlying disclosure, the method comprises a series of phases including:
Performing a first, or conditioning phase 100;
Performing a second, or controlled lesion cracking phase 101;
Performing a third, or mobilization phase 102, and
Performing a fourth, or lesion modelling phase 103.
Alternatively or supplementally, in the above method, the series of phases can further include:
Performing one or more drug delivery phase 104.
With respect to the foregoing,
the first, or conditioning phase 100 consists of ramping up the pressure of the inflatable member in 2 bar increments over a period of 1.5 minutes to a first pressure plateau of about 4 bar;
the second, or controlled lesion cracking phase 101 consists of ramping up the pressure in 2 bar increments over a period of 1.5 minutes from the first pressure plateau of about 4 bar to a second pressure plateau of about 8 bar;
the third, or mobilization phase 102 consists of ramping down the pressure from the second pressure plateau of about 8 bar to about 0 bar, and alternatingly modulating the pressure between 0 bar and a third pressure plateau of about 2 bar over a period of about 1.5 minutes, and
the fourth, or lesion modelling phase 103 consists of ramping up the pressure from the third pressure plateau of about 2 bar to a fourth pressure plateau of about 8 bar, and holding the pressure plateau for a period of 1 to 1.5 minutes, followed by ramping up the pressure to a fifth pressure plateau of about 10 to 12 bar and holding the pressure plateau for a period of 1 to 1.5 minutes, followed by slow deflation to an end pressure of 0 bar over a period of about 0.5 minutes.

Regarding the optional or supplemental phase of the series of phases, the drug delivery phase 104 consists of:
partially inflating the at least two lobes of the inflatable member to occlude a blood flow to an area to be treated;
administering therapeutic agents from the perfusion port across the drug perfusion lumen 51 and drug release opening 50 to a waist region 77 located in the area to be treated (65, 66);
maintaining a therapeutic treatment time;
withdrawing residual therapeutic agents into the drug perfusion lumen 51, and
deflating the at least two lobes 32, 34 of the inflatable member 13 to restore blood flow to the target treatment area.

In any of the above, the series of phases can include pressure regimes or profiles 107 applied with static and pulsatile pressure modulation. Further, the pulsatile pressure modulation can be performed in one or more phases.

The foregoing description, for purposes of explanation, refers to specific nomenclature to provide a thorough understanding of the invention. However, it will be apparent to one skilled in the art that the specific details are not required in order to practice the invention. The foregoing descriptions of specific implementations of the present invention are presented for purpose of illustration and description. They are not intended to be exhaustive or to limit the invention to the precise forms disclosed. Certainly many modifications and variations are possible in view of the above teachings. The embodiments are shown and described in order to best explain the principles of the invention and practical applications, to thereby enable others skilled in the art to best utilize the invention and various implementations with various modifications as suitable for the particular uses contemplated. It is intended that the scope of the invention be defined by the following claims and their equivalent.

We claim:

1. A balloon catheter comprising:
   an elongated member having a proximal end, a distal end, and at least one lumen extending at least partially through the elongated member; and
   an inflatable member proximally affixed to the elongated member adjacent to the distal end and in fluid communication with the at least one lumen, the inflatable member having a radius R and including at least two lobes, the at least two lobes separated from each other by one or more waist portions;
   wherein in an unpressurized state, the at least two lobes of the inflatable member are provided each folded and pleated, such that subsequent pressurization of the inflatable member individually unfolds each of the at least two lobes;
   wherein in a pressurized state, a segmentation of the inflatable member into the at least two lobes:
      distributes, and thereby reduces a torsional load that is transferred between the inflatable member and an area to be treated;
      controllably conveys opposing axial forces between the at least two lobes at the one or more waist portions, and thereby reduces an amount of axial load that is transferred between the inflatable member and the area to be treated; and
      controllably conveys equidirectional radial forces between the at least two lobes and around the one or more waist portions that differ in magnitude from the radial forces conveyed by the at least two lobes, thereby directing away radial stress from a vessel wall around the one or more waist portions;
   wherein the combination of the opposing axial and equidirectional radial forces around the one or more waist portions create variable directional forces that, when conveyed onto a portion of the area to be treated, controllably induce stress inflection points that result in the preferential formation of lesion fractures at each of said one or more waist portions of the inflatable member.

2. The balloon catheter according to claim 1, further comprising:
   a catheter tip;
   a kink-protection sleeve; and
   a manifold that further comprises:
   an inflation port; and
   a guide-wire port.

3. The balloon catheter according to claim 1, wherein the at least one lumen serves as:
   an inflation lumen that is in fluid communication with the inflatable member, and
   a guide-wire lumen, that extends at least partially through the elongated member, and connects the catheter tip to a guide-wire port.

4. The balloon catheter according to claim 1, wherein the elongated member is configured as a dual-lumen shaft and a dual-lumen configuration of the elongated member is selected from a group consisting of a parallel arrangement, a coaxial arrangement and a combination of coaxial and parallel arrangements.

5. The balloon catheter according to claim 1, wherein the elongated member is configured as a triple-lumen shaft and a triple-lumen configuration of the elongated member is selected from a group consisting of a parallel arrangement, a coaxial arrangement and a combination of coaxial and parallel arrangements.

6. The balloon catheter according to claim 1, wherein the one or more waist portions further includes one or more structural elements that reinforces at least one or more of the one or more waist portions, wherein the one or more structural elements that serve as a means for reinforcement of the at least one of the one or more waist portions are selected from a group consisting of a fiber, a seam, a thread, a ring, a tubing, an adhesive, a crosslinked polymer, a point-like, a line-like, a helical, a circular, a cylindrical, a semi-circular, an arced, a layered, and a interwoven attachment to the elongated member and combinations formed therefrom.

7. The balloon catheter according to claim 6, wherein the one or more structural elements are asymmetric.

8. The balloon catheter according to claim 6, wherein the one or more structural elements are arranged in a unidirectional orientation relative to a length axis of the inflatable member.

9. The balloon catheter according to claim 6, wherein the one or more structural elements are is arranged in a bidirectional orientation relative to a length axis of the inflatable member.

10. The balloon catheter according to claim 6, wherein the one or more structural elements are arranged in an alternating combination of unidirectional and bidirectional orientation relative to a length axis of the inflatable member.

11. The balloon catheter according to claim 1, wherein the one or more waist portions are of the inflatable member attached, partially attached and not attached to the elongated member.

12. The balloon catheter according to claim 1, wherein the one or more waist portions of the inflatable member comprises one or more length L selected from at least a set of ranges that includes 0-20 mm, 1-2 mm, 2-4 mm, 4-6 mm, 6-8 mm, 8-10 mm, 10-12 mm, 12-14 mm, 14-16 mm, 16-18 mm, and 18-20 mm.

13. The balloon catheter according to claim 1, wherein the one or more waist portions of the inflatable member comprises a length L not greater than two times the radius R in a pressurized state, so as to induce stress inflection points that result in the preferential formation of lesion fractures at each waist portion of the inflatable member.

14. The balloon catheter according to claim 1, wherein in a pressurized and lesion-contacting state, the one or more waist portions between the at least two lobes of the inflatable member and the area to be treated forms an impact zone that is substantially shaped as a trapezoid;
   wherein the trapezoid shape includes:
      an upper base having a first length that is equivalent to the length of the one or more waist portions;
      a lower base having a second length smaller than the first length;
      a first depth equivalent to a radial distance between the upper base and the lower base;
      a second depth equivalent to a radial distance between the lower base and a rotation axis of the inflatable member;
      two legs formed at an angle that is defined by the (first and second) lengths and radial distances between the lower and upper base, wherein a sum of the first and second depths are equivalent to an outer radius of the inflatable member, and wherein the first depth is equivalent to the depth of the one or more waist portions.

15. The balloon catheter according to claim 1, wherein a number of pleats of the at least two lobes of the folded and pleated inflatable member in an unpressurized state is an uneven number equal to or greater than three, a flap length of the at least two lobes of the folded and pleated inflatable member is from about a ratio between 0.25 to 0.75 of the radius of the inflatable member, and a maximum flap length of the inflatable member is determined by the first depth of the one or more waist portions, thereby reducing a torsional load that is transferred between the inflatable member and the area to be treated.

16. The balloon catheter according to claim 15, wherein at least one of the number of pleats and one of the flap length of the at least two lobes of the folded and pleated inflatable member in an unpressurized state are varied.

17. The balloon catheter according to claim 1, wherein a length of the inflatable member is selected from at least a set of ranges that includes 0-240 mm, 5-10 mm, 10-30 mm, 30-60 mm, 60-90 mm, 90-120 mm, 120-150 mm, 150-180 mm, 180-210 mm, and 210-240 mm.

18. The balloon catheter according to claim 1, wherein a length of the at least two lobes of the inflatable member is selected from at least a set of ranges that includes 0-240 mm, 1-5 mm, 5-10 mm, 10-30 mm, 30-60 mm, 60-90 mm, 90-120 mm, 120-150 mm, 150-180 mm, 180-210 mm, and 210-240 mm.

19. The balloon catheter according to claim 1, wherein the length of the at least two lobes of the inflatable member includes multiple, different lengths.

20. The balloon catheter according to claim 1, wherein a diameter of the at least two lobes of the inflatable member is selected from at least a set of ranges that includes 0-20 mm, 1-2 mm, 2-4 mm, 4-6 mm, 6-8 mm, 8-10 mm, 10-12 mm, 12-14 mm, 14-16 mm, 16-18 mm, and 18-20 mm.

21. The balloon catheter according to claim 20, wherein the diameter of the at least two lobes of the inflatable member includes multiple, different diameters.

22. The balloon catheter according to claim 20, wherein at least one of the length and one of the diameter of the at least two lobes are varied.

23. The balloon catheter according to claim 1, wherein the inflatable member further comprises a distal predilatation portion and a proximal dilatation portion wherein the pre-dilatation portion is consisting of at least four lobes, each length selected from a range of not greater than 1-10 mm; and each diameter in an unpressurized state selected from a range of not greater than 0.5-2 mm; and the dilation portion is consisting of at least four lobes, each length selected from a range of greater than 1-10 mm; and each diameter in a pressurized state selected from a range of greater than 0.5-2 mm.

24. The balloon catheter according to claim 1, wherein the inflatable member further includes:
a proximal and a distal end, each having a first wall thickness;
at least two lobes, each having a second wall thickness, and
one or more waist portions, each having a third wall thickness.

25. The balloon catheter according to claim 24, wherein the first wall thickness of the inflatable member exceeds the second wall thickness, and the second wall thickness exceeds the third wall thickness, thereby increasing flexibility at the one or more waist portions, and enhancing a magnitude of variable directional forces conveyed onto a portion of the area to be treated.

26. The balloon catheter according to claim 24, wherein the first wall thickness of the inflatable member exceeds the second wall thickness, and the third wall thickness exceeds the second wall thickness, thereby decreasing flexibility at the one or more waist portions, and reducing an amount of axial load that is transferred between the inflatable member and an area to be treated.

27. The balloon catheter according to claim 26; wherein a change of the third wall thickness of the one or more waist portions changes a magnitude and direction of the variable directional forces, such that the depth, direction, location and number of lesion fractures or fragmentation is reliably controlled.

28. The balloon catheter according to claim 27; wherein a third wall thickness at the one or more waist portions are of the at least two lobes of the inflatable member varied with respect to the first and second wall thickness, such that at least one of the axial stability and a magnitude and direction of the variable directional forces is reliably controlled.

29. The balloon catheter according to claim 1, for further medical use in complex lesion treatment.

* * * * *